(12) United States Patent
Fu et al.

(10) Patent No.: US 11,124,797 B1
(45) Date of Patent: Sep. 21, 2021

(54) WHEAT MALE-STERILITY GENE WMS AND ITS ANTHER-SPECIFIC EXPRESSION PROMOTER AND USES THEREOF

(71) Applicant: Shandong Agricultural University, Shandong (CN)

(72) Inventors: Daolin Fu, Shandong (CN); Mincheng Luo, Shandong (CN); Juan Qi, Shandong (CN); Fei Ni, Shandong (CN); Bo Lv, Shandong (CN); Shuyun Wang, Shandong (CN)

(73) Assignee: SHANDONG AGRICULTURAL UNIVERSITY, Shandong (CN)

( * ) Notice: Subject to any disclaimer, the term of this patent is extended or adjusted under 35 U.S.C. 154(b) by 74 days.

(21) Appl. No.: 15/579,058

(22) PCT Filed: Apr. 11, 2016

(86) PCT No.: PCT/IB2016/000537
§ 371 (c)(1),
(2) Date: Dec. 1, 2017

(87) PCT Pub. No.: WO2016/193798
PCT Pub. Date: Dec. 8, 2016

(30) Foreign Application Priority Data

Jun. 4, 2015 (CN) .......................... 201510303817.0

(51) Int. Cl.
C12N 15/82 (2006.01)
C12N 15/113 (2010.01)
C07K 14/415 (2006.01)

(52) U.S. Cl.
CPC ........ *C12N 15/8231* (2013.01); *C07K 14/415* (2013.01); *C12N 15/113* (2013.01); *C12N 15/8205* (2013.01); *C12N 15/8218* (2013.01); *C12N 15/8289* (2013.01)

(58) Field of Classification Search
CPC ................................................ C12N 15/8289
See application file for complete search history.

(56) References Cited

U.S. PATENT DOCUMENTS 8,629,322 B2 * 1/2014 Tanaka ..................... A01H 1/00
800/278

FOREIGN PATENT DOCUMENTS

| CN | 102533761 A | 7/2012 | |
| CN | 104911194 A | 9/2015 | |
| WO | WO-2013138309 A1 * | 9/2013 | ......... C12N 15/8289 |

OTHER PUBLICATIONS

Wu et al. Plant Cell Reports 21: 659-668 (2003).*
Cao et al. Genome 52: 95-99 (2009).*
Huang et al. Genetics 164: 655-664 (2003).*
Duan, J. et al. (Aug. 17, 2012), GenBank Accession JV88805.1 (Year: 2012).*
Canada Office action for Application No. 2,988,040, dated Dec. 5, 2018.
Office action for Canadian Patent Application No. 2,988,040, dated Aug. 13, 2019.
Liu, Xiuzhen et al. "Study of genes differential expression in wheat of Taigu genie male-sterile using DDRT-PCR" Acta Botanica Boreali-Occidentalia Sinica, vol. 23, No. 12, Dec. 31, 2003 (Dec. 31, 2003), pp. 2163-2166, (Abstract Only).
Duan, J. et al. "TSA: Triticum aestivum Ta_Contig15055.ansp mRNA sequence" Genbank Accession JV888005, Aug. 17, 2012 (Aug. 17, 2012).
Supplementary European Search Report for Application No. EP16802639, (dated Sep. 24, 2018).
"Experiment 8—Cloning the Promoter Region of the Gene of Interest (Gene Two)", Jan. 11, 2005 (Jan. 11, 2005), Retrieved from the Internet: URL:https://www.mcdb.ucla.edu/Research/Goldberg/HC70AL S05/pdf/Expt8protocol.pdf.
Office action for Eurasian Patent Application No. 201792344/28, dated Sep. 17, 2019.
European Office Action for Application No. 16 802 639.1-1118 dated Apr. 7, 2020.
Office action for Brazilian Patent Application No. BR112017025961-3, dated Jan. 8, 2020.
Office action for Japanese Patent Application No. 2017-559791, dated Feb. 12, 2020.
"TSA: Triticum aestivum Ta_Contig15055.ansp mRNA sequence", Aug. 17, 2012.
Sun, Zhengjuan, "The differentiation of protein expression of Ms2 in Taigu nuclear male-sterility wheat", Aug. 15, 2011, vol. D047, No. 49, pp. 1-69, (Abstract Only).
Eurasian Office Action dated Dec. 7, 2021.
Japanese Office Action dated Aug. 7, 2020.
Canadian Examination Report dated Sep. 2, 2020.
Ukrainian Application No. 201711536; Ukrainian Examination Report; dated Apr. 14, 2021; 6 Pgs.
India Application No. 201717038030; India Examination Report dated Mar. 16, 2021; 6 pgs.

* cited by examiner

*Primary Examiner* — Russell Kallis
(74) *Attorney, Agent, or Firm* — Tarolli, Sundheim, Covell & Tummino LLP

(57) ABSTRACT

The present invention provides a novel gene WMS conferring wheat male sterility, its anther-specific expression promoter, and uses of the same. In wheat, a well-known gene Ms2 causing dominant male sterility has been widely applied in recurrent selection in China. A RNA-seq approach was performed to reveal the anther-specific transcriptome in a pair of Ms2 isogenic lines, 'Lumai 15' and 'Lumai 15+Ms2'. As a result, a WMS gene was identified showing anther-specific expression at the early stage of meiosis and only in wheat carrying the Ms2 gene. The regulation of WMS could alter plant male fertility. The promoter of WMS was found to comprise anther-specific activity. Thus, the present invention might be used to achieve anther-specific gene expression, to develop male sterility in various plant species, to establish recurrent selection in various plant species, and to assist hybrid seed production.

7 Claims, 5 Drawing Sheets

Specification includes a Sequence Listing.

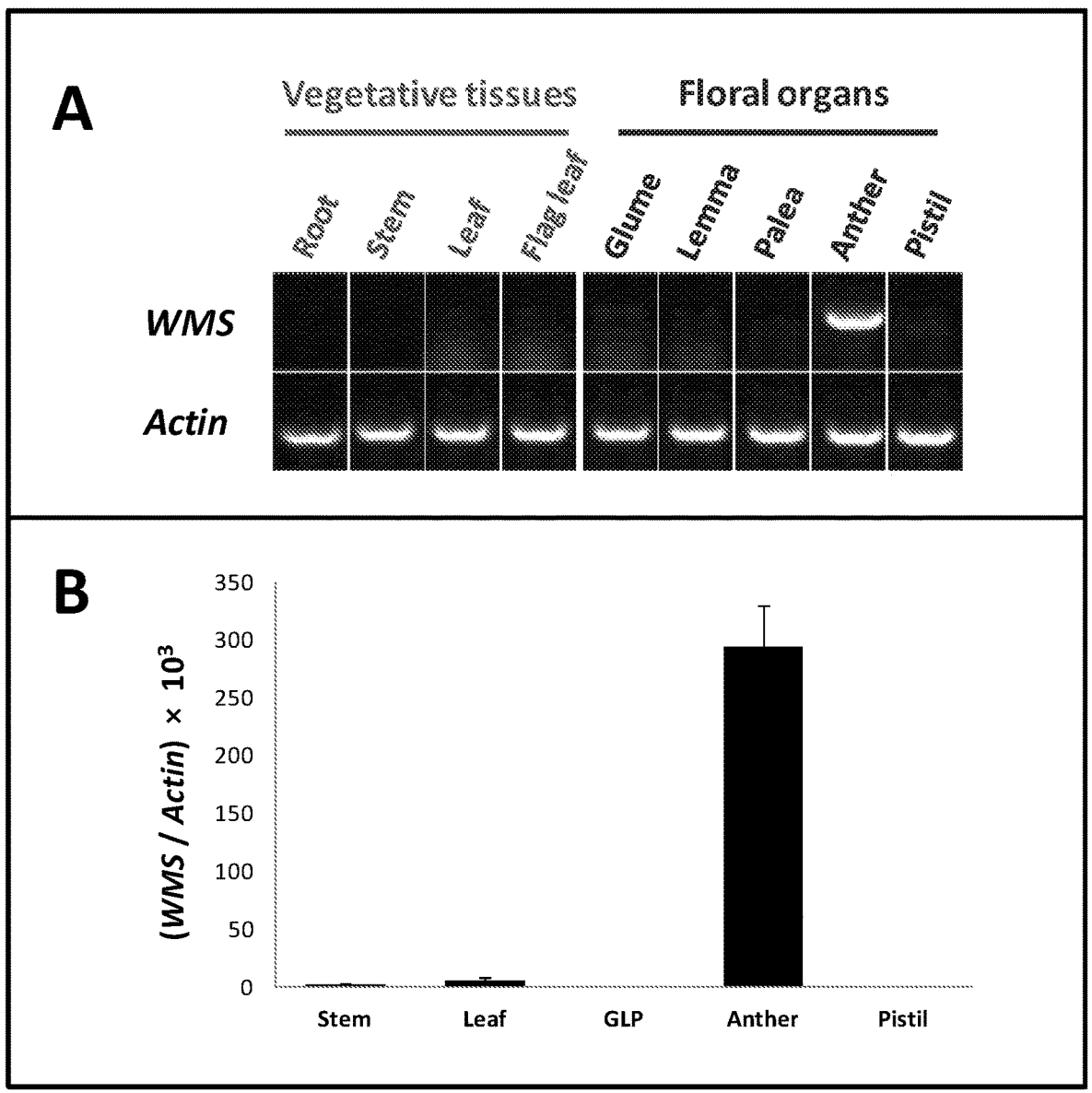
Figs. 3A-B

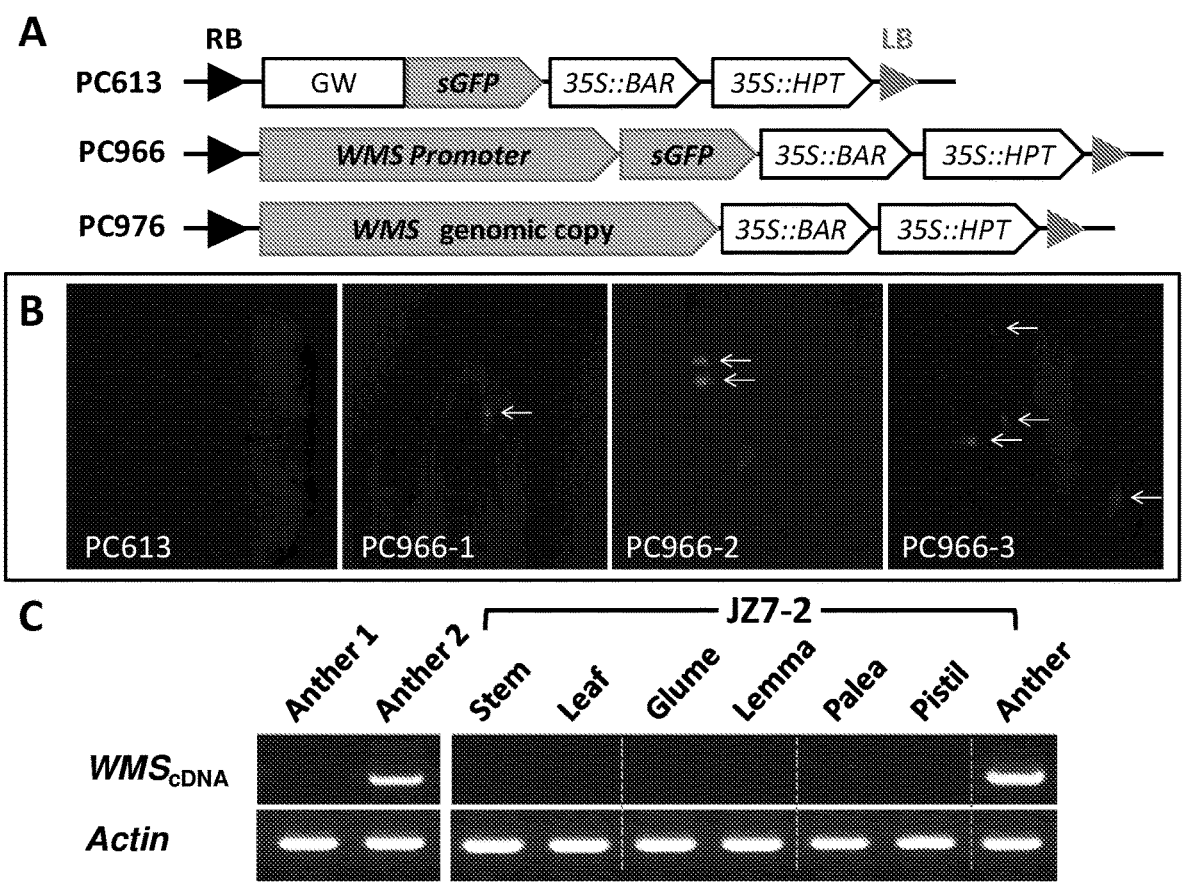
Figs. 4A-C

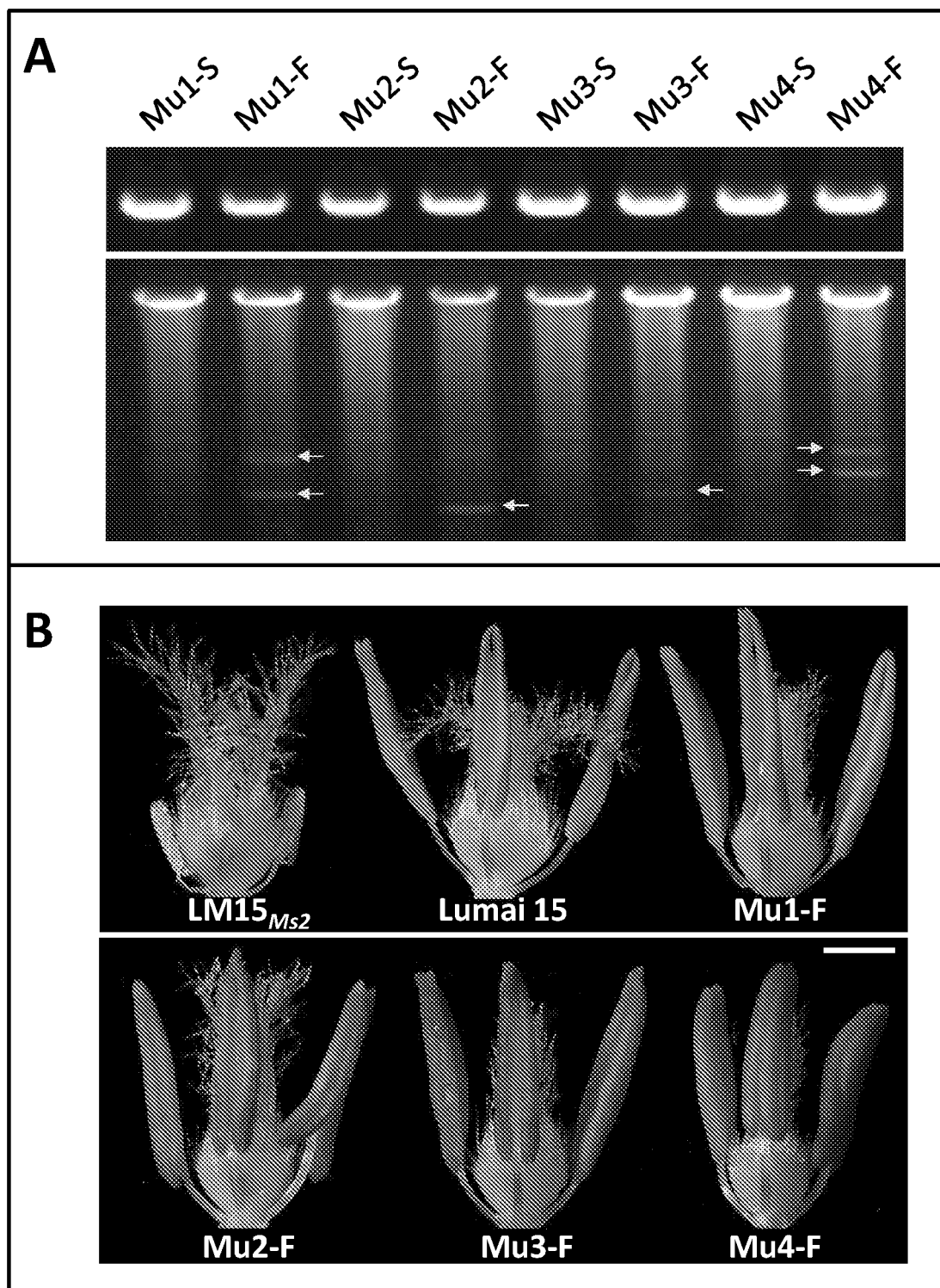
Figs. 5A-B

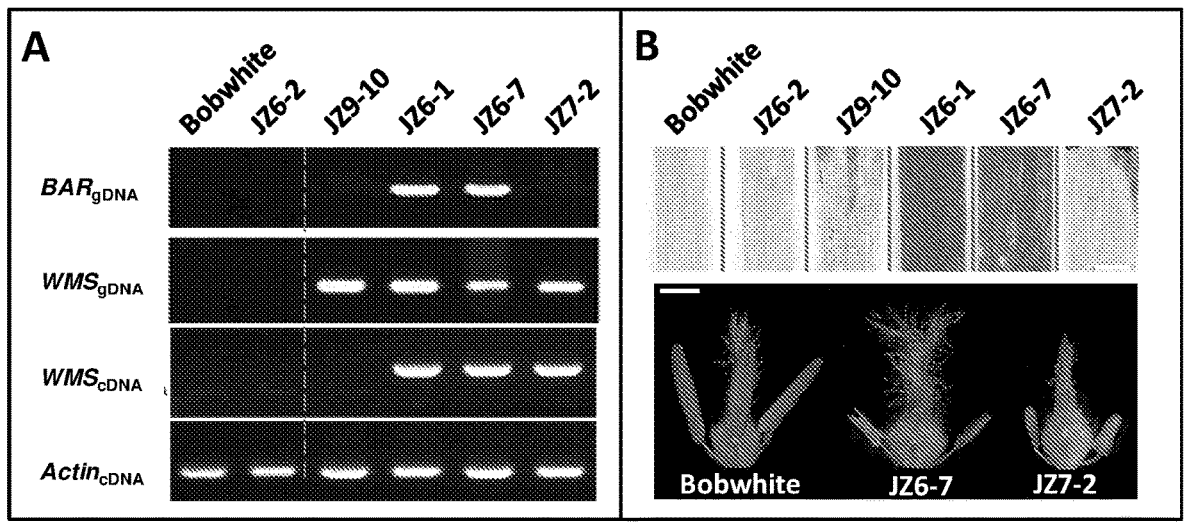
Figs. 6A-B
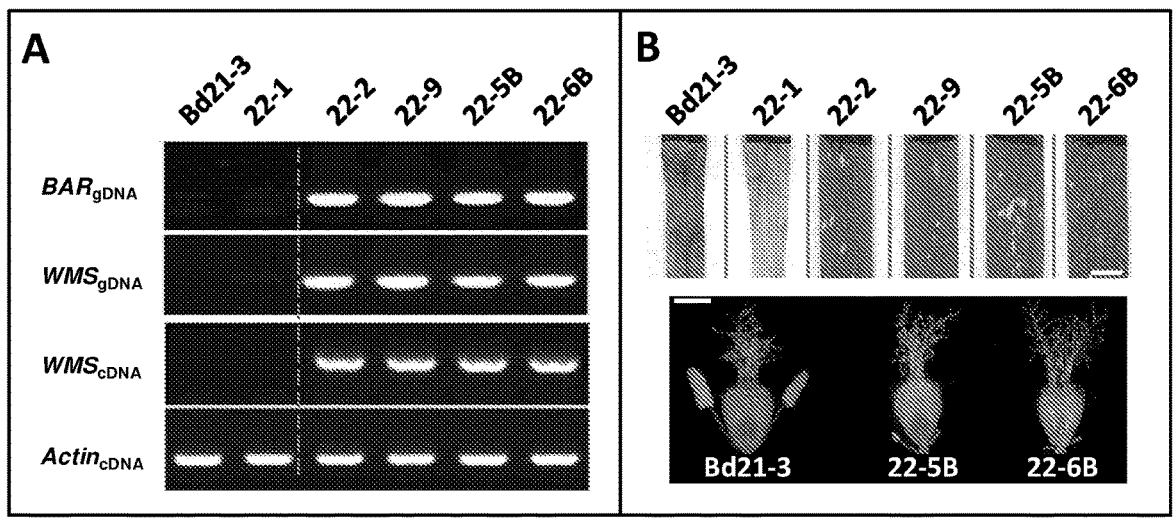
Figs. 7A-B

WHEAT MALE-STERILITY GENE WMS AND ITS ANTHER-SPECIFIC EXPRESSION PROMOTER AND USES THEREOF

RELATED APPLICATION

This application claims priority from Chinese Application No. 201510303817.0, filed Jun. 4, 2015, the subject matter of which is incorporated herein by reference in its entirety.

FIELD OF THE INVENTION

The present invention relates to one Wheat Male Sterility (WMS) gene, its anther-specific gene promoter, and uses of the same.

BACKGROUND OF THE INVENTION

The plant male sterility can be used to facilitate crossing for selective breeding and hybrid seed production (Rao et al., 1990; Kempken and Pring, 1999; Mackenzie, 2012). In many crop species, large numbers of male sterile strains have been discovered and preserved as valuable genetic resources, and there are numerous attempts to produce male sterile strains, especially in major cereal crops such as maize and rice.

The Pioneer Hi-Bred International develops the Seed Production Technology (SPT) (Waltz, 2012). In maize, the SPT technology integrates the use of the dominant Ms45 gene for male fertility, the recessive ms45 gene for male sterility, and the DsRed2 gene as a visual selection marker. The Ms45 gene is regulated by an anther-specific promoter. The maize maintainer line DP-32138-1 (ms45/ms45, Ms45-DsRed2/_) serves as a pollen donor to produce non-transgenic male-sterile maize lines (ms45/ms45), which are used as the female inbred parent to generate hybrid seeds. There are other studies on maize male sterility; mutagenesis of the cytochrome P450-like gene (Ms26) leads to the male sterilely in maize (Djukanovic et al., 2013). On the other hand, an anther-specific expression of target genes is crucial to create male sterility free from other unintended penalty. Luo et al. (2006) discovered a tapetum-specific gene RTS by differential screening of rice cDNA libraries (Luo et al., 2006). The RTS gene displays predominant expression in tapetum during meiosis and the expression disappears before anthesis. Liu et al. (2013) identified a rice anther-specific lipid transfer protein (OsLTP6) gene through high throughput expressional profiling (Liu et al., 2013). In general, anther specific expression of male fertility/sterility genes is important for introducing critical lines for hybrid seed production.

Genome editing allows specific modification of target genes in mammalian and other eukaryotic organisms (Cheng and Alper, 2014). More recently, the transcription activator-like effector nuclease (TALEN) and the clustered, regularly interspaced, short palindromic repeats (CRISPR)/Cas9 are proved to be functional in wheat (Wang et al., 2014) and barley (Wendt et al., 2013; Gurushidze et al., 2014). Therefore, genome editing can be used to introduce target-specific modification in cereal crops, which may be used to generate valued-added products.

Taigu genic male sterile wheat (henceforth referred to as 'Taigu') is a male-sterile hexaploid wheat mutant discovered in China (Yang et al., 2009). A single dominant gene Ms2 determines male sterility in 'Taigu'. When 'Taigu' wheat is crossed with male-fertile hexaploid wheat, their $F_1$ plants segregate on the male fertility/sterility: half male-fertile plants and half male-sterile plants (Deng and Gao, 1982). Phenotypic (dwarfing conferred by Rht-D1c) and molecular makers have been developed for the Ms2 locus (Liu and Deng, 1986; Cao et al., 2009). Since 1983, the 'Taigu' wheat has been used as a tool for recurrent selection in China. Up to date, hundreds of Chinese wheat lines have been developed to carry the Ms2 gene or the tightly linked Rht-D1c/Ms2 locus (henceforth referred to as RMs2), collectively designated 'Taigu wheat'. By 2010, forty-two wheat cultivars with improved disease resistance, salt and drought tolerance, or yield performance have been released via the RMs2-based recurrent selection. In order to manipulate the Ms2 gene for a better production system, we aimed to clone the Ms2 gene using transcriptome analysis.

SUMMARY OF THE INVENTION

The present invention provides a novel Wheat Male Sterility (WMS) gene, its gene promoter, and uses of the same.

The present invention utilized RNA-seq to characterize the anther transcriptome of 'Lumai 15' and 'Lumai 15+Ms2' (henceforth $LM15_{Ms2}$) at the early meiosis stage. As a result, one WMS gene was identified, which displayed an anther-specific expression at the early stage of meiosis and only in wheat carrying a dominant Ms2 gene. The WMS gene was suggested to be involved in male sterility in wheat, and the manipulation of WMS gene in plants might alter plant fertility. In addition, the WMS promoter was thought to comprise anther-specific activity, which is important to achieve anther-specific gene expression. Thus, the present invention can be said to be highly valuable when used as a tool to achieve anther-specific gene expression, to develop male sterility in various plant species, to establish recurrent selection in various plant species, and to assist seed production. Specifically, the present invention relates to the following:

[1] an isolated DNA of any one of the following (a) to (e): (a) a cDNA comprising the nucleotide sequence of SEQ ID NO: 1; (b) a DNA encoding the amino acid sequence of SEQ ID NO: 2; (c) a DNA comprising the nucleotide sequence of SEQ ID NO: 6; (d) a DNA encoding a protein which is (i) functionally equivalent to a protein comprising the amino acid sequence of SEQ ID NO: 2, and (ii) comprises the amino acid sequence of SEQ ID NO: 2, wherein one or more amino acids are substituted, deleted, added, and/or inserted; and (e) a DNA that (i) encodes a protein which is functionally equivalent to the protein comprising the amino acid sequence of SEQ ID NO: 2, and (ii) hybridizes under stringent conditions to the DNA comprising the nucleotide sequences of SEQ ID NOs: 1 and 6;

[2] a DNA encoding an antisense RNA that is complementary to the transcription product of the DNA of SEQ ID NOs: 1 and 6;

[3] a DNA encoding an RNA that comprises ribozyme activity that specifically cleaves the transcription product of the DNA of SEQ ID NOs: 1 and 6;

[4] a DNA encoding an RNA that down-regulates expression of the DNA of SEQ ID NOs: 1 and 6 by the co-suppression effect when expressed in plant cells;

[5] a DNA encoding a RNA that comprises a characteristic that is dominant-negative for an endogenous transcripts in plant cells encoded by the DNA of [1]; or a DNA encoding a protein that comprises a characteristic that is dominant-negative for an endogenous protein in plant cells encoded by the DNA of [1];

[6] a vector comprising a DNA of any one of [1] to [5];

[7] a transformed plant cell to which a DNA of any one of [1] to [5] or the vector of [6] is introduced;

[8] a transformed plant comprising the transformed plant cells of [7];

[9] a transformed plant clone or offspring of the transformed plants of [8], once the clone or offspring containing the transformed plant cells of [7];

[10] a seed, tissue and organ from the transformed plants of [8] or [9], once they contain the transformed plant cells of [7];

[11] a DNA of any one of the following (a) to (c) that comprises anther-specific promoter activity: (a) a DNA comprising the nucleotide sequence of SEQ ID NO: 5; (b) a DNA comprising the nucleotide sequence of SEQ ID NO: 5, wherein one or more nucleotides are substituted, deleted, added, and/or inserted; and (c) a DNA that hybridizes under stringent conditions to the DNA comprising the nucleotide sequence of SEQ ID NO: 5;

[12] a vector comprising the DNA of [11];

[13] a transformed plant cell comprising the DNA of [11] or [12];

[14] a transformed plant comprising the transformed plant cells of [13];

[15] a transformed plant clone or offspring of the transformed plants of [14], once the clone or offspring containing the transformed plant cells of [13];

[16] a seed, tissue and organ from the transformed plants of [14] or [15], once they contain the transformed plant cells of [13];

[17] a genetically modified plant cell generated by genome editing and/or induced mutagenesis on DNAs comprising the nucleotide sequences of SEQ ID NOs: 1 and 4, once these modifications regulate plant male fertility;

[18] a genetically modified plant comprising the genetically modified plant cells of [17];

[19] a plant clone or offspring of the genetically modified plants of [18], once the clone or offspring containing the modified plant cells of [17]; and

[20] a seed, tissue and organ from the genetically modified plants of [18] or [19], once they contain the modified plant cells of [17].

BRIEF DESCRIPTION OF THE DRAWINGS

FIG. 3 depicts the anther-specific expression of the WMS gene. A) RT-PCR was performed to detect the WMS cDNA in anther, glume, leaf, lemma, palea, pistil, root, and stem. B) qRT-PCR was performed to measure the cDNA levels of WMS in anther, GLP (glume, lemma, and palea), leaf, pistil, and stem. Actin was included as controls in both RT-PCR and qRT-PCR analyses.

FIG. 4 confirms the anther-specific activity of the WMS promoter. A) Plasmids were prepared to study the promoter activity; PC613 was a destination vector carrying the gateway compatible GFP cassette; PC966 carried the $P_{WMS}$:: GFP expression cassette where the $P_{WMS}$ represented the WMS promoter (SEQ ID NO: 5); PC976 carried a genomic copy of the WMS gene (SEQ ID NO: 7); all three vectors had the same plasmid backbone of pCAMBIA1300. B) Transient expression of GFP fluorescence in wheat anthers; arrows indicated the green fluorescence signals. C) RT-PCR was performed to detect the WMS cDNA in anther, glume, leaf, lemma, palea, pistil and stem in wheat transgenic plant 'JZ7-2' (Table 3), which was derived from genetic transformation with PC976; there were also two controls including Anther 1 from 'Lumai 15' and Anther 2 from 'Lumai 15$_{Ms2}$'. Bar=100 μm.

FIG. 5 shows the TILLING screening and fertile anthers of $M_1$ plants carrying induced mutations in the dominant WMS gene. A) The presence of a dominant WMS gene was confirmed by PCR analysis using WMS-FP12 and WMS-RP12 (top panel); TILLING detection of the WMS mutation using primers WMS-FP8 and WMS-RP8 in selected $M_1$ plants (S: sterile tiller; F: fertile tiller; arrows indicated the Cel1 digested band; lower panel). B) Development of fertile anthers in selected $M_1$ mutants of the WMS gene. 'Lumai 15' and 'Lumai 15$_{Ms2}$' were included as controls. Bar=1.5 mm.

FIG. 6 shows genetic complementation of the dominant WMS gene in 'Bobwhite'. A) PCR analysis confirmed genomic intergration (BAR and WMS) and cDNA expression (WMS and Actin) in the $T_0$ generation. B) BAR-based bioassay for herbicide resistance (top panel; Bar=2.5 mm); the expression of WMS cDNA caused a male-sterile phenotype in transgenic $T_0$ plants (lower panel; Bar=1.5 mm). 'Bobwhite' acted as the wild type control.

FIG. 7 shows genetic complementation of the dominant WMS gene in Brachypodium 'Bd21-3'. A) PCR analysis confirmed genomic intergration (BAR and WMS) and cDNA expression (WMS and Actin) in the $T_0$ generation. B) BAR-based bioassay for herbicide resistance (top panel; Bar=2.5 mm); the expression of WMS cDNA caused a male-sterile phenotype in transgenic $T_0$ plants (lower panel; Bar=0.5 mm). The Brachypodium 'Bd21-3' was included as the wild type control.

DETAILED DESCRIPTION OF THE INVENTION

Figure 1:
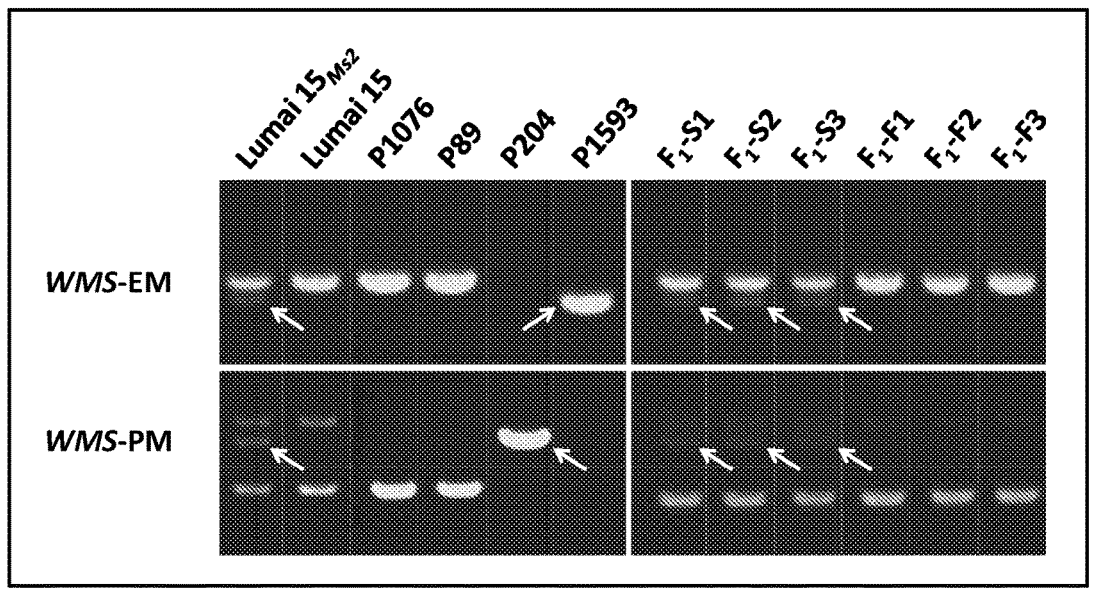
FIG. 1 depicts genotyping by the WMS-EM and WMS-PM markers. Top panels represented genotyping by the WMS-EM marker, lower panels of genotyping by the WMS-PM marker; left panels were genotypes of common wheat (parental lines) and BAC clones, right panels of genotypes of $F_1$ individuals from the 'LM15$_{Ms2}$'/'Lumai 15' combination. In $F_1$ plants, six representative plans were displayed, including three male-sterile plants (S1, S2 and S3) and three male-fertile plants (F1, F2 and F3). Arrows indicated the specific bands that segregated with the male sterility trait.

The present invention provides DNAs encoding the WMS protein. The nucleotide sequence of the WMS cDNA in 'Taigu wheat' is set forth in SEQ ID NO: 1, the amino acid sequence of the protein encoded by the WMS cDNA is set forth in SEQ ID NO: 2, the full-length nucleotide sequence including promoter, transcriptable fragment, and terminator of the WMS gene in 'Taigu wheat' is set forth in SEQ ID NO: 4, the nucleotide sequence of the WMS promoter in 'Taigu wheat' is set forth in SEQ ID NO: 5, and the nucleotide sequence of the transcriptable fragment of the WMS gene in 'Taigu wheat' is set forth in SEQ ID NO: 6.

The present invention comprises cDNA and genomic DNA that encode the WMS protein. One skilled in the art can prepare the cDNA and genomic DNA using conventional methods. cDNA can be prepared by: for example, a) extracting mRNA from 'Taigu wheat' (e.g., 'LM15$_{Ms2}$'); b)

synthesizing cDNA using the mRNA as template; c) amplifying the WMS cDNA using PCR primers specific to the cDNA of the present invention (e.g., SEQ ID NO: 1); d) cloning the PCR product into vectors. Equally, genomic DNA can be prepared by extracting it from 'Taigu wheat', constructing a genomic library (where BAC, cosmid, fosmid, and such can be used as a vector), and then screening positive clones using DNA fragments of the present invention (e.g., SEQ ID NO: 4). The genomic DNA can also be prepared by PCR-based cloning on DNAs of the present invention (e.g., SEQ ID NO: 4).

The present invention includes DNAs that encode proteins functionally equivalent to the WMS protein from Taigu wheat (e.g., SEQ ID NO: 2). Herein, "proteins functionally equivalent to the WMS protein from Taigu wheat" means target proteins that comprise a biological or biochemical function equivalent to the WMS protein of the present invention (e.g., SEQ ID NO: 2). Examples include the induction of plant sterility. To evaluate whether a test gene can induce male sterility, 'Taigu wheat' can be mutagenized via the EMS-induced mutagenesis as demonstrated in Example 7, and the knockout and knockdown mutants of the test gene can be identified by TILLING as demonstrated in Example 8. The test gene induced male sterility can be validated using genetic complementation in the male-fertile wheat 'Bobwhite'. For example, the genomic allele of WMS (SEQ ID NO: 7) can be introduced into 'Bobwhite' using biolistics bombardment as demonstrated in Example 9. In addition, it is feasible to the introduce the genomic allele of WMS (SEQ ID NO: 7) into the model plant Brachypodium using *Agrobacterium*-mediated transformation as demonstrated in Example 10. The resulting plant phenotypes can be analyzed.

Other example of such a function is the anther-specific expression, which is characterized by predominant expression in the anther that is at least five times or more, preferably ten times or more, and more preferably 15 times or more than its expression in other tissues listed in Example 5. To evaluate whether a test gene is specifically transcribed in a plant's anther, mRNAs can be extracted from various types of plant tissues, and cDNA will be synthesized from these mRNAs. The quantitative reverse-transcription PCR (qRT-PCR) can be used to measure the cDNA amount of the test gene in different types of plant tissues as demonstrated in Example 5.

DNAs that encode proteins functionally equivalent to the WMS protein (SEQ ID NO: 2) are preferably derived from monocotyledons, more preferably from Gramineae, and most preferably from Triticeae species. Such DNA include, for example, alleles, homologues, variants, derivatives, and mutants of the current invention (SEQ ID NO: 1 or SEQ ID NO: 6), which encode a protein comprising the amino acid sequence of SEQ ID NO: 2, in which one or more amino acids are substituted, deleted, added, or inserted.

Genome editing can be used to knock out target genes in plants and animals (Cheng and Alper, 2014). A number of genome editing techniques involving the zinc-finger nuclease (ZFNs), the transcription activator-like effector nuclease (TALEN)) and the clustered, regularly interspaced, short palindromic repeats (CRISPR) have been successfully used to in wheat (Shan et al., 2014; Wang et al., 2014) and barley (Wendt et al., 2013; Gurushidze et al., 2014). Genome editing normally leads to single or multiple base deletion or insertion in the target region of interested, and those occurred among the coding exons may cause amino acid change or protein truncation (Wang et al., 2014). So long as a DNA derived from genome editing encodes a protein functionally equivalent to a natural WMS protein (SEQ ID NO: 2), that DNA can be included as a DNA of the present invention, even if the introduced WMS protein includes one or more amino acid substitutions, deletions, additions, or insertions. The DNAs of the present invention also include conservative mutants in which nucleotides are mutated without resulting in mutation of the protein amino acid sequence (conservative mutations).

For those skilled in the art, it is feasible to modify the WMS gene and its homologues of the current invention (SEQ ID NOs: 1 and 6) using genome editing. In addition, it is feasible to introduce the target mutation via induced mutagenesis or by natural germplasms screening. For example, Slade et al. (2005) developed wheat EMS-induced mutant population and then successfully identified target mutations using the method of targeting induced local lesions in genomes (TILLING) (Slade et al., 2005). In addition, the germplasms pool evolves with large amount of spontaneous mutations, it is feasible to identify target mutation in germplasms collection using Ecotilling (Till et al., 2006). For those skilled in the art, it is easy to develop plant mutant populations and then identify mutations in the DNA (SEQ ID NOs: 1 and 6) of the current invention. At the same time, it is easy to identify the spontaneous mutations of the DNA (SEQ ID NOs: 1 and 6) of the current invention in germplasms pool or breeding lines/cultivars. Therefore, the current invention also covers: (a) using genome editing, induced-mutagenesis, and natural screening to generate plant cells that mutation(s) on the DNA (SEQ ID NOs: 1 and 6) of the current invention; (b) a plant carrying the type of plant cells of (a); (c) a plant clone or offspring of the type of plants of (b), once they contain the type of plant cells of (a); (d) a seed, tissue and organ from clone or offspring in (b) and (c), once they contain the type of cell in (a).

Other methods for preparing DNAs that encode proteins functionally equivalent to the WMS protein (SEQ ID NO: 2) include polymerase chain reaction (PCR) (Saiki et al., 1985; Hemsley et al., 1989; Landt et al., 1990), recombinant DNA technology, and artificial gene synthesis (Kosuri and Church, 2014), which are well known to those skilled in the art. Namely, it is routine experimentation for one skilled in the art to isolate DNAs highly homologous to the WMS gene from wheat or other plants by using PCR primers that specifically hybridize to a nucleotide sequence of the WMS gene (SEQ ID NOs: 1 and 6), or by using a fragment of the WMS gene (SEQ ID NOs: 1 and 6) as a problem to screen DNA and cDNA libraries. DNAs, which are isolated using PCR technology, recombinant DNA technology, artificial gene synthesis, and such, and which encode proteins functionally equivalent to the WMS protein (SEQ ID NO: 2), are also included in the DNAs of the present invention. At the amino acid level, DNAs thus isolated are thought to be highly homologous to the amino acid sequence of the WMS protein (SEQ ID NO: 2). High homology means sequence identity, over the entire amino acid sequence, of at least 50% or more, preferably 70% or more, and more preferably 90% or more (for example, 95%, 96%, 97%, 98%, and 99% or more).

Amino acid and nucleotide sequence identity can be determined using the BLAST algorithm (Altschul et al., 1990; Karlin and Altschul, 1993). Based on this algorithm, programs called BLASTN, BLASTP, BLASTX, TBLASTN, and TBLASTX were introduced (Korf et al., 2003). BLASTN searches a nucleotide database using a nucleotide query; BLASTP searches protein database using a protein query; BLASTX searches protein database using a translated nucleotide query; TBLASTN searches translated nucleotide database using a protein query; TBLASTX searches translated nucleotide database using a translated nucleotide query. The fundamental steps of these analysis methods are publicly available (http://blast.ncbi.nlm.nih.gov/Blast.cgi).

Screening of the genomic DNA or cDNA libraries may utilize the Southern blotting technology (Southern, 1975). Southern blotting involves two major steps. The first step is to attach DNA fragments to nitrocellulose or nylon membrane, and the second step is to perform hybridization between labeled proble DNA and the DNA fragment attached to the membrane. During washing, it is necessary to adjust washing stringency by controlling temperature, salt content, and time. The stringency increases along with the reduction of salt content in the SCC buffer (20×, 10×, 6×, 2×, 1×, 0.5×, 0.2×, 0.1×), the increase of temperature (42° C., 50° C., 55° C., 60° C., 65° C., 70° C., 75° C.) and the increase of washing time (1 min, 2 min, 5 min, 10 min, 15 min, 20 min, 30 min). In the current invention, 'high stringency' indicates a washing step will be performed in diluted SCC buffer (≤1×), under high temperature (≥55° C.) and for extended duration (≥10 min).

For application, the DNAs (SEQ ID NOs: 1 and 6) that encode the WMS protein of the present invention are also thought to be useful in granting sterility to male fertile plants. In other words, it is thought sterility can be granted to male fertile plants by inserting a DNA (SEQ ID NOs: 1 and 6) encoding the WMS protein of the present invention into a suitable vector, introducing this vector into plant cells that are capable to form male-fertile plants, regenerating the resulting recombinant plant cells, and then reproducing the transgenic plants that comprise the characteristic of male sterility. Since male-sterile plants cannot self-pollinate, it is necessary to maintain them using pollens from other male-fertile plants. On the other hand, the DNAs (SEQ ID NOs: 1 and 6) that encode the WMS protein of the present invention are also thought to be useful in granting fertility to male-sterile plants conferred by the WMS gene. In other words, it is thought fertility can be granted to male-sterile plants by inserting the antisense RNA (asRNA) and/or the hairpin RNA (hpRNA) of the DNA (SEQ ID NO: 1) encoding the WMS protein of the present invention into a suitable vector, introducing this vector into plant cells that are capable to form male-sterile plants, and then regenerating the resulting recombinant plant cells. Since male-sterile varieties cannot self-pollinate, attempting to maintain them is difficult, even when those varieties comprise desirable traits. However, if fertility can be recovered using the antisense gene and/or the hairpin RNA of the DNA (SEQ ID NOs: 1 and 6) that encodes the WMS protein, self-pollination becomes possible, as does the maintenance of desirable traits.

The antisense nucleic acids regulate target gene expression via transcriptional interference, RNA masking, double-stranded RNA (dsRNA)-dependent mechanisms and chromatin remodeling (Lapidot and Pilpel, 2006). The antisense sequences used in the present invention can inhibit the expression of a target gene by any of the above actions. As one embodiment, an antisense sequence designed to be complementary to an untranslated region close to the 5' end of the mRNA of a gene will be effective in inhibiting translation of that gene. However, a sequence complementary to a coding region, or to a 3'-end untranslated region can also be used. In this way, DNAs comprising antisense sequences of a gene's translated regions as well as untranslated regions are included in the antisense DNAs that can be used for the DNA (SEQ ID NO: 1) of the present invention.

An antisense DNA to be used herein is ligated downstream of an appropriate promoter such as the maize ubiquitin (Ubi) promoter (Christensen et al., 1992) or the WMS promoter (SEQ ID NO: 5), and a sequence comprising a transcription termination signal is preferably ligated to the 3' end of the DNA. DNAs thus prepared can be introduced into a desired plant using known methods. Antisense DNA sequences are preferably sequences complementary to an endogenous gene, or a part thereof of the plant to be transformed, but need not be perfectly complementary as long as they can effectively inhibit gene expression. The transcribed RNA is preferably 90% or more, and more preferably 95% or more (for example, 96%, 97%, 98%, 99%, or more) complementary to the transcribed products of the target gene. In order to effectively inhibit target gene expression using an antisense sequence, an antisense DNA should comprise at least 15 nucleotides or more, preferably 100 nucleotides or more, and even more preferably 500 nucleotides or more. Antisense DNAs to be used are generally less than 5 kb, and preferably less than 2.5 kb long.

Suppression of endogenous gene expression can also be carried out using of the DNA that encodes the target gene (Hammond et al., 2001; Paddison et al., 2002). To express the hpRNA in plant cells, a DNA matrix designed to form hairpin RNA or drive RNA interference (RNAi) can be linked to a promoter sequence such as the Ubi promoter and a transcription termination sequence. By using hpRNA or RNAi technology, the transcription products of the target genes of the present invention can be specifically down-regulated, and the gene expression can be suppressed.

Suppression of endogenous gene expression may also be achieved by co-suppression resulting from transformation with a DNA comprising a sequence identical or similar to a target gene sequence (Smyth, 1997; Ketting and Plasterk, 2000). The term "co-suppression" refers to the phenomenon of suppression of expression of both the introduced exogenous gene and the target endogenous gene when a gene comprising a sequence identical or similar to that of the target endogenous gene is introduced into plants by transformation. For example, to obtain a plant in which the WMS gene is co-suppressed, plants of interest are transformed with a vector DNA constructed to express the WMS gene (SEQ ID NOs: 1 and 6), or a DNA comprising a similar sequence, and plants with suppressed male sterility compared to wild type plants are selected from the plants thus obtained. Genes to be used for co-suppression do not have to be completely identical to the target gene, however should comprise sequence identity of at least 70% or more, preferably 80% or more, more preferably 90% or more (for example, 95%, 96%, 97%, 98%, 99%, or more). Sequence identity may be determined using an above-described method.

In addition, suppression of endogenous gene expression in the present invention can also be achieved by transforming a plant with a gene comprising characteristics that are dominant-negative to the target gene. A gene comprising dominant-negative characteristics is a gene that, when expressed, comprises the function of eliminating or reducing the activity of an original endogenous gene of the plant. In Brachypodium, microRNA (miRNA) miR5200 cleaves the mRNA of the flowering time gene FT, and the overexpression of miR5200 delays flowering time in Brachypodium (Wu et al., 2013). Some miRNA or small interfering RNA (siRNA) may target to WMS and its homologues. It is also possible to design artificial microRNA (amiRNA) that targets to WMS and its homologues. Collectively, it is possible to manipulate the production of effective amiRNA, miRNA, and siRNA to regulate the mRNA accumulation of WMS and its homologues in order to control plant male fertility.

Vectors that can be used in plant cell transformation are not particularly limited as long as they can express the inserted gene in plant cells. For example, vectors that comprise promoters for expressing genes in specific plant tissues (e.g., the promoter of the present invention as SEQ ID NO: 5) and promoters for constitutively expressing genes in plant cells (e.g., the Ubi promoter) can be used. In addition, vectors comprising a promoter which is activated upon induction by an external stimulus can also be used. Herein, "plant cells" comprise various forms of plant cells, for example, suspension culture cells, protoplasts, plant sections, and calli, of various plant species.

A vector can be introduced to a plant cell using various methods known to those skilled in the art, such as polyethylene glycol methods, electroporation methods, *Agrobacterium*-mediated methods, and particle bombardment methods. Regeneration of plants from transformed plant cells is also possible using methods known to those skilled in the art, according to the type of plant cells. In plants, for example, many techniques for producing recombinant plants are already established, and are widely used in the field of the present invention. These methods include the method for introducing genes into protoplasts using polyethylene glycol and then regenerating plants, the method for introducing genes into protoplasts using electric pulse and then regenerating plants, the method for directly introducing genes into cells using particle bombardment method and then regenerating plants, and the method for introducing genes via an *Agrobacterium* and then regenerating plants. These methods can be appropriately used in the present invention.

Once transformant plants, into which the genome of a DNA of the present invention has been inserted, are obtained, it is possible to obtain offspring from these plants by sexual or asexual reproduction. From these plants, their offspring, or their clones, reproductive materials can be obtained (seeds, calli, protoplasts, etc). Using these materials, these plants can be mass-produced. The present invention comprises plant cells introduced with DNAs covered by the present invention, plants comprising those cells, the offspring or clones of those plants, and the reproductive materials of those plants, their offspring, and their clones. Therefore, the current invention covers: (a) transgenic plant cells carrying DNA of the current invention; (b) a plant carrying the type of plant cells of (a); (c) a plant clone or offspring of the type of plants of (b), once they contain the type of plant cells of (a); (d) a seed, tissue and organ from clone or offspring in (b) and (c), once they contain the type of cell in (a).

The fertility/sterility of plants produced in this way can be expected to differ from that of wild type plants. For example, wheat 'Bobwhite' is male fertile, but the expression of the DNA (e.g., SEQ ID NO: 4) confers male sterility to transgenic Bobwhite. On the other hand, once the expression of DNA (e.g., SEQ ID NO: 4) in Taigu wheat has been suppressed, by the introduction of antisense DNA or the like, are thought to be invested with male fertility. In plants, the methods of the present invention can be used to regulate fertility/sterility so as to suppress self-pollination and force cross-pollination, thereby granting the valuable characteristic of hybrid vigor.

The present invention presents DNA comprising anther-specific promoter activity. An example of this kind of DNA is a genomic DNA (SEQ ID NO: 4) upstream of the start codon in the DNA (SEQ ID NO: 5) encoding the WMS protein in the current invention. The promoter DNAs of the present invention include DNAs highly homologous to the nucleotide sequence of SEQ ID NO: 5, so long as they comprise anther-specific promoter activity. An example of these types of DNA is a DNA with anther-specific promotor activity, comprising the nucleotide sequence of SEQ ID NO: 5, where one or more nucleotides are substituted, deleted, added, or inserted. The DNA promoters of the present invention are preferably derived from monocotyledons, more preferably derived from Gramineae, and most preferably derived from Triticeae species. However, so long as they comprise anther-specific promoter function, their derivation is not particularly limited.

The above WMS protein-coding DNAs of the present invention can be used for isolating DNAs comprising anther-specific promoter activity. For example, genomic DNAs upstream of a DNA encoding the WMS protein of the present invention can be acquired by using a DNA (SEQ ID NO: 6) of the present invention, or a part of it, as a probe to screen a genomic DNA library. Since these upstream genomic DNAs are thought to comprise anther-specific promoter activity, they have high industrial value when used to specifically express arbitrary genes in the anther. "An arbitrary gene" means a DNA whose transcription can be induced by a DNA promoter (SEQ ID NO: 5) of the present invention. "An arbitrary gene" can be any coding and no-coding DNA fragments, of which the non-coding DNAs may comprise ribozyme activity, or may be used to generate amiRNA, asRNA, hpRNA, miRNA, siRNA and so on. These DNA fragment will present anther-specific expression pattern under the WMS promoter (SEQ ID NO: 5). In addition, since the DNAs that encode the WMS protein of the present invention are expressed specifically in plant anthers, they are also thought to be useful as markers to identify the anther tissue in whole floral dissections.

DNAs highly homologous to the nucleotide sequence of SEQ ID NO: 5 can also be obtained using PCR techniques (Saiki et al., 1985), recombinant DNA technology, and artificial gene synthesis (Kosuri and Church, 2014). For example, by using a DNA comprising the nucleotide sequence of SEQ ID NO: 5 or a part thereof as a template, and using oligonucleotides that specifically hybridizes to a DNA molecule (SEQ ID NO: 5) as PCR primers, DNAs highly homologous to the nucleotide sequence of SEQ ID NO: 5 can be isolated from wheat and other plant species.

Methods well known to those skilled in the art can be used to prepare this kind of DNA. For example, genome editing techniques, which are well-known in the art (Cheng and Alper, 2014), can be used for introducing mutations including one or more base substitutions, deletions, additions, or insertions to DNA comprising the nucleotide sequence of SEQ ID NO: 5. Mutations can also be introduced using site-directed mutagenesis, mutagen/radiation induced mutagenesis, and PCR methods (Saiki et al., 1985; Hemsley et al., 1989; Landt et al., 1990).

Known reporter assays using reporter genes or such can be used to investigate whether or not DNAs prepared as described above comprise anther-specific promoter activity. The reporter gene is not particularly limited, so long as its expression can be detected. For example, reporter genes generally used by those skilled in the art include the luciferase gene (LUC), β-glucuronidase gene (GUS), and green fluorescence gene (GFP), etc. The expression level of the reporter gene can be determined using methods known to those skilled in the art, according to the type of reporter gene. For example, the expression level of the luciferase gene as a reporter can be determined by measuring the fluorescence of a fluorescent compound, caused by the catalytic action of the luciferase gene expression product. The expression level of the GUS gene can be determined by analyzing the coloring of 5-bromo-4-chloro-3-indolyl-.beta.-glucuronide (X-Gluc) or the luminescence of Glucuron (ICN), caused by the catalytic action of the GUS gene expression product. The expression level of the GFP gene can be determined by measuring fluorescence due to the GFP protein.

The promoter DNAs of the present invention can be used to express an arbitrary gene in an anther-specific manner by: for example, (a) constructing a vector comprising a promoter DNA of the present invention; (b) operably linking the arbitrary gene downstream of the promoter DNA of the present invention in that vector of (a); (c) generating transgenic plant cells carrying the WMS promoter (SEQ ID NO: 5) or the vector of (b); and (d) obtaining transgenic plants containing transgenic plant cells of (c). "Operably linking" means binding an arbitrary gene to a promoter DNA of the present invention such that it can be expressed in response to the activation of the promoter DNA of the present invention. Since the promoter DNA of the present invention comprise high anther-specific activity, it is preferable that the arbitrary genes are genes that can be particularly expressed in the anther. For example, the WMS of the present invention that relates to sterility/fertility of wheat can be suitably used. General genetic engineering techniques can be used to construct a vector comprising a promoter DNA of the present invention. There is no particular limitation as to the plant cells to which the vector is introduced. The above-mentioned methods, known to those skilled in the art, can be used to introduce vectors to plant cells, to regenerate transformed plant cells to plants, etc.

Therefore, the present invention covers: (a) genetically modified plant cells with the promoter DNAs covered by the present invention; (b) plants comprising the type of cells of (a); (c) the offspring or clones of the plants of (b), once they contain the type of cells of (a); (d) a seed, tissue and organ from clone or offspring in (b) and (c), once they contain the type of cell in (a).

For those skilled in the art, it is feasible to modify the WMS promoter (SEQ ID NO: 5) and its homologous sequence using genome editing, introduce mutation(s) to the WMS promoter (SEQ ID NO: 5) and its homologous sequence using mutagenesis, or identify the natural spontaneous mutation on the WMS promoter (SEQ ID NO: 5) and its homologous sequence. Therefore, the current invention covers: (a) genetically modified plant cells with variation on the WMS promoter (SEQ ID NO: 5) obtained by genome editing, mutagenesis, and natural screening; (b) plants comprising the type of cells of (a); (c) the offspring or clones of the plants of (b), once they contain the type of cells of (a); (d) a seed, tissue and organ from clone or offspring in (b) and (c), once they contain the type of cell in (a).

In summary, the current invention contains the WMS gene (SEQ ID NOs: 1 and 6), WMS homologues, and their promoter (e.g., SEQ ID NO: 5). Another specific expression of the WMS gene (SEQ ID NOs: 1 and 6) is able to grant the regular male-fertile plants with male sterility. By suppressing WMS gene expression in plants, it is possible to grant the regular male-sterile plants the characteristic of male fertility. In addition, since the WMS gene promoter is thought to comprise anther-specific activity, it is useful to express arbitrary genes in an anther-specific manner. As expected, the application of the WMS (SEQ ID NOs: 1 and 6), its homologues, and their promoters (e.g. SEQ ID NO: 5) will greatly advance plant breeding and seed industry.

Hereinbelow, the present invention will be specifically described using Examples, but it is not to be construed as being limited thereto.

EXAMPLES

The present invention was based on a pair of Ms2 isogenic wheat lines 'Lumai 15' and 'LM15$_{Ms2}$', which were developed by the Shandong Agricultural University. Wheat plants were maintained in a greenhouse under 16 h photoperiod (105 µmol m$^{-2}$ s$^{-1}$) with day temperature of 25-30° C. and night temperature of 15-20° C. Water, regular chemicals and plant hormones were from Fisher Scientific (Pittsburgh, Pa., USA) and Sigma-Aldrich (St. Louis, Mo., USA), plant tissue culture media from PhytoTechnology Laboratories (Overland Park, Kans., USA), microbial growth media from BD (Becton, Dickinson and Company, Franklin Lakes, N.J., USA), and antibiotics from Gold Biotechnology (St. Louis, Mo., USA). PCR Primers of the current invention are listed in Table 1.

TABLE 1

PCR primers used in the current invention

| Primer ID | Primer sequence (5' to 3') | Sequence ID No. |
|---|---|---|
| WMS-RP1 | AGGTTTGCTTGAGTTCCTCCCG | SEQ ID NO: 8 |
| WMS-RP2 | CCTTGTGGTGATGAGCGTGAAG | SEQ ID NO: 9 |
| WMS-FP1 | CGGGAGGAACTCAAGCAAACCT | SEQ ID NO: 10 |
| WMS-FP2 | GAGTGGTTCACGTGCTGATTAC | SEQ ID NO: 11 |
| WMS-FP3 | CAGTACCCGCAGTGGACAC | SEQ ID NO: 12 |
| WMS-RP3 | TAAATCACAGGCAGGATTTGATAAAC | SEQ ID NO: 13 |
| WMS-FP4 | CCGTCAGCACACTGTACTTCA | SEQ ID NO: 14 |
| WMS-RP4 | CGATGTAGAGCCTCAAATCC | SEQ ID NO: 15 |
| WMS-FP5 | CACATGTTTGCGCTCGAAATG | SEQ ID NO: 16 |
| WMS-RP5 | AAGAAACGAGCCGTCCAGTA | SEQ ID NO: 17 |
| WMS-FP6 | CGCAGTGGACACACGCTTAGCTT | SEQ ID NO: 18 |
| WMS-RP6 | TGAGTTGGAGTTGGTCCCCATC | SEQ ID NO: 19 |
| WMS-FP7 | TCTCAGAAACGAGCCCCAAGT | SEQ ID NO: 20 |
| WMS-RP7 | GAACCATCCCTGGTCGATGT | SEQ ID NO: 21 |
| WMS-FP8 | GGCTCTGATACCAAATGTTGTTG | SEQ ID NO: 22 |
| WMS-RP8 | ATGGTGGTGTGCCCCTAAAAAG | SEQ ID NO: 23 |
| WMS-FP9 | GCTTGAAACTGCTGGTATATATG | SEQ ID NO: 24 |
| WMS-RP9 | GTAATCAGCACGTGAACCACTC | SEQ ID NO: 25 |
| WMS-FP10 | TGTTCCTGGATTCGTGAGTGG | SEQ ID NO: 26 |
| WMS-RP10 | CGATCTCCGTGTCCATGTGCTAC | SEQ ID NO: 27 |

TABLE 1-continued

PCR primers used in the current invention

| Primer ID | Primer sequence (5' to 3') | Sequence ID No. |
| --- | --- | --- |
| WMS-FP11 | GCGGCCGCGGGTGAGGCTTTGCCAAGG | SEQ ID NO: 28 |
| WMS-RP11 | GGCGCGCCCGATCTCCGTGTCCATGTGCT | SEQ ID NO: 29 |
| WMS-RP12 | CGTAGATGCGGACCCAGGGGAT | SEQ ID NO: 30 |
| BAR-FP1 | AAGCACGGTCAACTTCCGTA | SEQ ID NO: 31 |
| BAR-RP1 | GAAGTCCAGCTGCCAGAAAC | SEQ ID NO: 32 |
| Actin-FP1* | TCAGCCATACTGTGCCAATC | SEQ ID NO: 33 |
| Actin-RP1* | CTTCATGCTGCTTGGTGC | SEQ ID NO: 34 |
| Actin-FP2 | GCCATGTACGTCGCAATTCA | SEQ ID NO: 35 |
| Actin-RP2 | AGTCGAGAACGATACCAGTAGTACGA | SEQ ID NO: 36 |

Note:
To facilitate gene cloning, the restriction enzyme site NotI was included in the PCR primer WMS-FP11, and the AscI site was added to the PCR primer WMS-FP11. Restriction enzyme sites were highlighted using underlines.
*RT-PCR primers Actin-FP1 and Actin-RP1 worked on wheat and *Brachypodium* cDNA samples.

Example 1

Transcriptome Analysis Reveals a Gene Showing Anther-Specific Expression

RNA sequencing (RNA-seq) involves direct sequencing of cDNAs using high-throughput DNA sequencing technologies (Nagalakshmi et al., 2001). A RNA-seq approach was performed to reveal the anther-specific transcriptome in a pair of Ms2 isogenic lines, 'Lumai 15' and 'LM15$_{Ms2}$'. The auricle distance between the flag and penultimate leaves was used as criteria for selecting anthers at the similar development stage. Anthers, pistils, and flag leaves were separately collected from a main stem or tiller on which an auricle distance reached four centimeters. For anthers, three replications were prepared for 'Lumai 15' and 'LM15$_{Ms2}$', respectively. For pistils, three replications were prepared by pooling equal amount of tissues from 'Lumai 15' and 'LM15$_{Ms2}$', as well as for flag leaves. Total RNAs were extracted using the Trizol method (Life Technologies, Grand Island, N.Y., USA) and submitted for RNA-seq provided by Berry Genomics Company (Beijing, China).

Sequencing libraries were prepared for an average insert size of 500 bp. Paired end (PE) sequencing was performed for two lanes of 125-base paired reads on HiSeq2500 (Illumina, San Diego, USA). Raw data were pre-processed using Trimmomatic (Bolger et al., 2014), and clean data were acquired after eliminating the adapter, low quality bases (half or more bases of a read with a quality value Q≤3), and unknown bases (unknown bases of a read >3%). de novo transcriptome assembly of clean data was performed using Trinity (Haas et al., 2013). Transcript abundance was estimated using RSEM (Li and Dewey, 2011), and differentially expressed transcripts/genes were identified using the edger program (Robinson et al., 2010). In general, many genes were associated with higher expression in anthers from 'LM15$_{Ms2}$' than in anthers from 'Lumai 15'. In particular, an unknown gene (SEQ ID NO: 1) showed specific expression in 'LM15$_{Ms2}$', but undetectable in 'Lumai 15', which was hypothesized to confer wheat male sterility (WMS) in 'LM15$_{Ms2}$'. The unknown gene, now designated as WMS, was chosen for functional analysis.

Example 2

Cloning of the Full-length cDNA of the WMS Gene

Total RNAs from anthers of 'LM15$_{Ms2}$', an aliquot of RNAs submitted for RNA-seq, were used to prepare cDNAs using the RevertAid Frist Strand cDNA Synthesis Kit (Thermo Scientific, Waltham, Mass., USA). The 5' and 3' cDNA ends of the WMS gene (SEQ ID NO: 1) were identified from 'LM15$_{Ms2}$' by RACE PCR using the SMARTer RACE cDNA Amplification ket (Clontech Laboratories, Mountain View, Calif., USA). The 5' RACE PCR involved the use of two WMS primers, WMS-RP1 and WMS-RP2, where WMS-RP2 was nested to WMS-RP1. The 3' RACE PCR involved the use of another two WMS primers, WMS-FP1 and WMS-FP2, where WMS-FP2 was nested to WMS-FP1. Sequencing of the 5' and 3' RACE PCR products validated the full-length status of the WMS gene assembled during RNA-seq analysis. Accordingly, a full-length cDNA of WMS was cloned from 'LM15$_{Ms2}$' using the WMS primers, WMS-FP3 and WMS-FP3, which agreed to the nucleotide sequence of SEQ ID NO: 1. The 1,485-bp cDNA contains an 882-bp open reading frame (ORF). Two in-frame stop codons in the 5' end of the cDNA proposed that the predicted ORF is reliable. In the present invention, the upstream region adjacent to the predicted start codon was considered as the promoter of the WMS gene.

Example 3

Construction of the Genomic BAC Library on 'LM15$_{Ms2}$'

A bacterial artificial chromosome (BAC) library was constructed for 'LM15$_{Ms2}$' using standard protocols (Luo and Wing, 2003; Shi et al., 2011). In brief, high-molecular weight (HMW) genomic DNA was extracted from leaf tissues, partially digested using the restriction enzyme HindIII, and separated on 1% agarose by pulsed-field gel electrophoresis (PFGE); DNA fragments in the range of 100-300 kb were recovered from the agarose gel, re-selected by running PFGE again, ligated into the BAC vector pIndigoBAC536-S which was opened by HindIII and dephosphorylated; the ligation product was transformed into the *E coli* DH10B T1 Phage-Resistant Cells (Invitrogene, Carlsbad, Calif., USA); transformants were selected on LB medium with 12.5 mg/L of chloramphenicol, 80 mg/L X-gal, 100 mg/L IPTG; white colonies were individually picked into 384-well microtiter plates.

As a result, 706,176 BAC clones were picked and arranged in 1,839 384-well plates (Table 2). Quality test on 337 randomly selected BAC clones revealed an average insert size of 124.6 kb and an empty rate of 0.50%. Therefore, the 'LM15$_{Ms2}$' BAC library represented a 5.5-fold coverage of the wheat genome (~16 Gb).

TABLE 2

The BAC library of wheat 'LM15$_{Ms2}$'

| Batch codes | Plate quantity | Clones tested | Empty Rate (%) | Insert size (kb) | Clone quantity | Genome coverage | Proportion of library (%) |
|---|---|---|---|---|---|---|---|
| A | 1,112 | 106 | 0.00 | 118.0 | 427,008 | 3.149 | 57.81 |
| B | 330 | 123 | 0.81 | 132.2 | 126,720 | 1.047 | 19.22 |
| C | 255 | 77 | 2.59 | 147.6 | 97,920 | 0.903 | 16.58 |
| D | 142 | 31 | 0.00 | 102.1 | 54,528 | 0.348 | 6.39 |
| Total | 1,839 | 337 | 0.50 | 124.6 | 706,176 | 5.5 | 100 |

Example 4

Screening and Sequencing of BAC clones of 'LM15$_{Ms2}$'

A PCR-based screening procedure was developed for the 'LM15$_{Ms2}$' BAC library. The BAC library was first duplicated by inoculating a new set of 384-well plates, a primary plasmid pool was prepared from the culture of each duplicated plate using the ZR BAC DNA Miniprep Kit (Zymo Research Corporation, Irvine, Calif., U.S.A.), and a super plasmid pool was made by pooling equal amount of plasmid DNA from ten primary plasmid pools. In total, 1,839 primary plasmid pools were prepared, and 184 super plasmid pools were made.

In order to screen the BAC library, multiple PCR primers were designed matching the cDNA sequence of WMS gene (SEQ ID NO: 1), and were then tested whether they would work on genomic DNAs from 'Lumai 15' and 'LM15$_{Ms2}$'. As a result, WMS-FP4 and WMS-RP4 amplified a single fragment in 'Lumai 15', but two fragments in 'LM15$_{Ms2}$', where the larger fragment of 'LM15$_{Ms2}$' ran to the same level in 1% agarose gel as the fragment of 'Lumai 15' (FIG. 1). Apparently, the smaller fragment was specific to 'LM15$_{Ms2}$', most likely from the Ms2 region which leads to male sterility in 'Taigu wheat'. Indeed, the smaller fragment cosegregated with male sterility in a large segregation population (ca. 5000 plants), for which the seeds were harvested from the male-sterile plants of 'LM15$_{Ms2}$' that were pollinated by pollen grains from the male-fertile plants of 'Lumai 15', and the population segregated approximately half male-fertile and half male-sterile. Therefore, an exon-derived PCR marker, WMS-EM, was developed by using the WMS-FP4 and WMS-RP4 primers.

Figure 2:
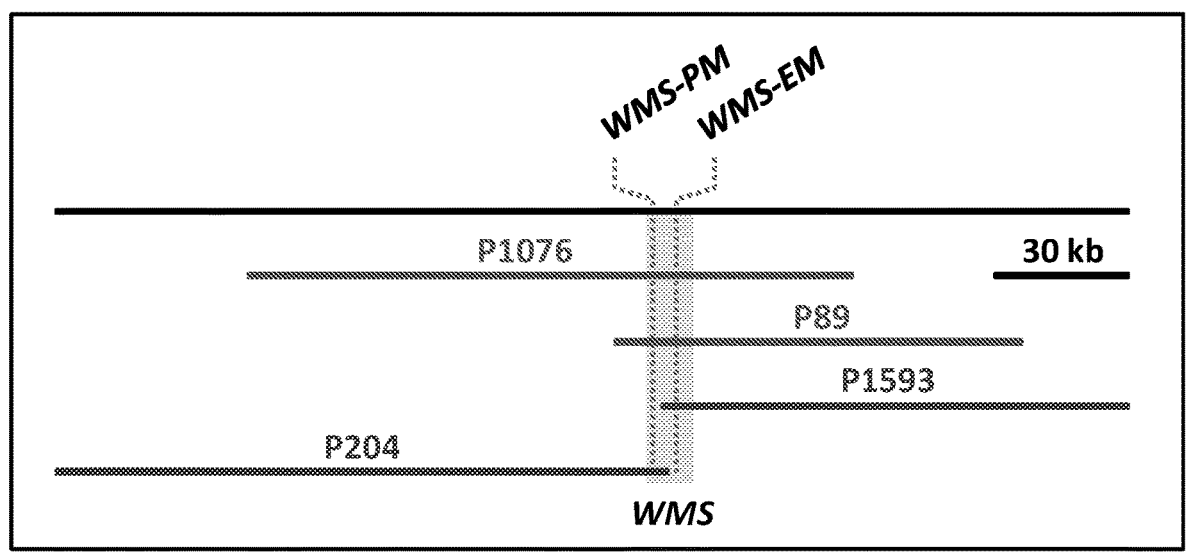
FIG. 2 depicts BAC clones carrying the WMS/wms gene. P89 and P1076 were derived from the 4D chromosome carrying a recessive wms gene; P204 and P1593 were derived from the 4D chromosome carrying a dominant WMS gene. The region with gray shading represents the full expression matrix of WMS gene (e.g., SEQ ID NO: 4) in the present invention. The insert size of each BAC clone is in scale.

The WMS-EM marker was used to screen the super plasmid pools and then the primary plasmid pools of the 'LM15$_{Ms2}$' BAC library. Once a primary pool was identified, the BAC clone would be determined using the 384-well PCR. In total, three BAC clones were recovered (FIG. 2), including one clone giving smaller PCR product and two clones generating larger PCR product. Most likely, BAC clones (P89 and P1076) giving larger PCR product were generated from the 4D chromosome lacking the dominant Ms2 gene, while the BAC clone (P1593) giving smaller PCR product was generated from the 4D chromosome carrying the dominant Ms2 gene (FIG. 1). The WMS-EM marker of P1593 was completely linked to male sterility, suggesting a dominant WMS gene on P1593, while the WMS-EM marker of P89/P1076 did not show tight association with male sterility, suggesting a recessive wms gene on P89/P1076. All three BAC clones were chosen for next generation sequencing provided by the Berry Genomics Company. The raw sequence data was pre-processed by eliminating adapters, low quality bases (half or more bases of a read with a quality value Q≤5), and unknown bases (unknown bases of a read >10%). BAC vector (pIndigoBAC536-S) and E. coli. genomic DNA was de-contaminated using the cross match tool of the Phrap package (Ewing et al., 1998). de novo assembly of clean data was performed for different K-mer size (21-91) by the ABySS 1.5.2 program (Simpson et al., 2009). A K-mer value of 41 was chosen for sequence assembly, which corresponded to the best N50 value. Sequence analysis revealed that P89 and P1076 shared a 54,056 bp identical fragment, representing the same chromosome, but they were substantial polymorphisms between P89/P1076 and P1593. According to the WMS cDNA (SEQ ID NO: 1), all three BACs contained a complete transcriptable region of the WMS/wms gene, the predicted WMS cDNA of P1593 was identical to the nucleotide sequence of SEQ ID NO: 1, but there were eleven single nucleotide polymorphisms (SNPs) between the predicted wms cDNA of P89/P1076 and the nucleotide sequence of SEQ ID NO: 1. In comparison, the wms gene in P89 and P1076 was complete with sequence information of promoter (SEQ ID NO: 3), but the WMS gene in P1593 was incomplete because it sited on one BAC end leading to an incomplete promoter (FIG. 2).

Therefore, multiple PCR primers were designed to match the wms promoter (SEQ ID NO: 3), and were then tested whether they would work on genomic DNAs from 'Lumai 15' and 'LM15$_{Ms2}$'. As a result, WMS-FP5 and WMS-RP5 amplified two bands in 'Lumai 15', but three bands in 'LM15$_{Ms2}$', where the smaller fragment of 'LM15$_{Ms2}$' ran to the same level in 1% agarose gel as the fragment of 'Lumai 15' (FIG. 1). Apparently, the larger fragment was specific to 'LM15$_{Ms2}$'. Therefore, a promoter-derived PCR marker, WMS-PM, was developed by using the WMS-FP5 and WMS-RP5 primers. The WMS-PM marker was used to screen the 'LM15$_{Ms2}$' BAC library. An additional BAC clone P204 was identified (FIGS. 1 and 2), which was derived from the 4D chromosome with the dominant Ms2 gene. Again, the BAC clone P204 was sequenced and assembled, which shared a 1,212 bp overlap with the BAC clone P1593. In comparison, the wms gene (SEQ ID NO: 3) is 8,657 bp, but the corresponding sequence of the WMS gene is 10, 592 bp (SEQ ID NO: 4), the size difference is mainly due to the transposon insertions in the WMS promoter.

Example 5

Analysis of Tissue-Specific Expression of WMS Gene

Both reverse-transcription PCR (RT-PCR) and qRT-PCR were used to measure the mRNA level of WMS gene in each wheat tissue. RT-PCR involved the use of two WMS primers, WMS-FP6 and WMS-RP6, and two primers, Actin-FP1 and Actin-RP1, for the Actin control. qRT-PCR involved the use of two other WMS primers, WMS-FP7 and WMS-RP7, and two primers, Actin-FP2 and Actin-RP2, for the Actin control (Fu et al., 2007). The WMS gene was specifically expressed in wheat anthers, but not in other tissues such as glume, leaf, lemma, palea, pistil, root, and stem (FIG. 3A); the mRNA levels of WMS in the anther was 100 times more prominent than in any other tested tissues (FIG. 3B).

Example 6

Identification of the WMS Promoter

The DNA region upstream to the predicted start codon was analyzed by comparing these of the dominant WMS and recessive wms. To recover a functional promoter, a relatively long fragment (2 to 4 kb) is considered for plant genes, especially those unknown genes. In the present invention, a 3502 bp fragment (SEQ ID NO: 3) was considered as the promoter for the recessive wms gene in 'Lumai 15'. The corresponding region of the dominant WMS gene from 'LM15$_{Ms2}$' was 5578 bp (SEQ ID NO: 4). The selected promoters of WMS and wms shared 2414 bp identical bases at the 5' end, but the rest 1088 bp of the wms promoter displayed substantial variations when compared to the rest 3164 bp of the WMS promoter. The size increase in the WMS promoter was mainly caused by two transposon insertions of 275 bp and 1791 bp, respectively. Presumably, the 5578 bp upstream region of the WMS gene was thought to comprise the anther specific activity.

To verify the anther-specific activity of the WMS promoter (SEQ ID NO: 5), two plant expression constructs were prepared, including the destination vector PC613 and the GFP reporter construct PC966 (P$_{WMS}$::GFP) (FIG. 4A), here P$_{WMS}$ represents the WMS promoter (SEQ ID NO: 5). The GFP gene in PC613 and PC966 was derived from pGWB4 (Nakagawa et al., 2007). Both PC613 and PC966 had the same plasmid backbone of pCAMBIA1300. The DNA linker between P$_{WMS}$ and GFP was 5'-TAGG-GAGAGGCGCGCCGACCCAGCTTTCTTGTA-CAAAGTGGTGATCATG-3' (SEQ ID NO: 37), the 5' bases TAGGGAG were derived from the end of the WMS promoter, and the 3' end ATG stands for the start codon of GFP. PC613 and PC966 were bombarded into different floral origans (lemma, palea, pistil and anther) as instructed in Example 9. GFP fluorescence was observed under stereo fluorescence microscope three days post bombardment. GFP signals were detected in tissues bombarded with construct PC966 (P$_{WMS}$::GFP), especially in anther, but not in tissues bombarded with the construct PC613. Therefore, WMS promoter (SEQ ID NO: 5) in current innovation has promoter activity and can promote GFP expression in anther.

To perform genetic complementation (Example 9) and to validate the function of the WMS promoter (SEQ ID NO: 5), the WMS genomic allele (SEQ ID NO: 7) was cloned and used to assemble a plant expression construct PC976 (FIG. 4A). Vector construction and particle bombardment were performed as illustrated in Example 9. Both PC966 and PC976 utilized identical fragment of the WMS promoter (SEQ ID NO: 5). Tissue-specific expression of the WMS gene was documented in the transgenic wheat line 'JZ7-2' (Table 3), which involved the use of the WMS WMS primers, WMS-FP6 and WMS-RP6, and the Actin primers, Actin-FP1 and Actin-RP1. As a result, the WMS promoter (SEQ ID NO: 5) of the current innovation conferred anther-specific expression of the WMS gene, but not in other tissues including leaf, stem, glume, lemma, palea and pistil (FIG. 4C). In conclusion, the WMS promoter (SEQ ID NO: 5) has anther-specific expression activity.

Therefore, it is feasible to assemble an expression cassette containing the WMS promoter (SEQ ID NO: 5) and a target gene. The expression cassette, once introduced into plants (such as cereal crops, woods, vegetables and flowers), will confer anther-specific expression of the target gene. This will be important for generating male sterility and other important traits in plants.

Example 7

Development of the EMS Population of 'Lumai 15$_{RMs2}$'

The mutant population of 'LM15$_{Ms2}$', containing 1, 200 WMS-positive M$_1$ plants, were created using the 87.4 μM solution of Ethyl methanesulfonate (EMS; Sigma-Aldrich, St. Louis, Mo.). In brief, every 400 seeds (M$_0$) from the cross 'LM15$_{Ms2}$'/'Lumai 15' were soaked in 100 ml of 87.4 μM EMS (0.9% in water, v/v), and were then incubated in a running shaker at 150 rpm and under 25° C. for 10 h. After the EMS treatment, seeds were washed under running water at room temperatures for 4 h. Mutagenized M$_1$ seeds were set on wet papers and maintained in a plastic box (length×width×height=40 cm×30 cm×20 cm) covered by plastic wrap, and then incubated under 25° C. and 16 h photoperiod for 8 d. Vigorous seedlings with roots were transplanted to soil and maintained in a cold room under 4° C. and 12 h photoperiod for 6 w. The vernalized M$_1$ plants were then maintained in a greenhouse under 25° C. and 16 h photoperiod. In greenhouse, only plants carrying a dominant WMS gene were maintained, but those lacking the dominant WMS were discarded, which generated a mutant population including 1200 WMS-containing M$_1$ plants.

Example 8

TILLING Screening of the WMS Mutation in EMS Population of 'LM15$_{Ms2}$'

Because of the presence of a dominant WMS gene, all 1200 WMS-containing M$_1$ plants are supposed to be male-sterile. However, some mutations on the WMS gene are thought to abolish its function, causing a male-fertile characteristic. Therefore, the characteristics of male fertility/sterility were investigated in all spikes of the 1200 WMS-containing M$_1$ plants. Out of 3138 spikes inspected, twenty spikes displayed male-fertile phenotypes, characterized by regular anther, pollen dispersal, and seed setting (FIG. 5).

Genomic DNA was prepared from the main-stem associated flag leaf of the M$_1$ plants using the Sarkosyl method (Yuan et al., 2012). DNA concentrations were measured using a Nanodrop spectrophotometer (Thermo Scientific, Wilmington, Del., USA) and normalized to 100 ng μl$^{-1}$. Equal amount of DNAs were pooled fourfold and organized into 96-well format. DNA samples were also prepared from the flag leaves of main stems or tillers that produced male-fertile spikes. Each of these DNAs was pooled twofold with equal amount of genomic DNA from the wild type 'LM15$_{Ms2}$'.

Total genomic DNA was extracted using the Sarkosyl method (Yuan et al., 2012). For all plants, a flag leaf segment (3-5 cm in length) of the primary tiller was used to prepare independent DNA samples. DNA concentration was measured by the ND2000 spectrophotometer (Thermo Scientific, Wilmington, Del., USA) and was adjusted to 100 ng/μl using ddH$_2$O. Every four DNA samples were pooled together and stored in 96-well plates. For the twenty tillers/spikes showing male-fertile phenotype, their flag leaves were collected to prepare independent DNA samples. Once a male-fertile tiller happened to be a primary tiller, DNA sample of the primary tiller was used instead. Each DNA from a male-fertile tiller was then equally pooled with the DNA of wild type 'LM15$_{Ms2}$' and stored in 96-well plate as well.

A modified TILLING approach (Uauy et al., 2009) was used to detect induced mutations of the WMS gene. The polyacrylamide detection method involves a two-step screening approach. The first PCR screen involves two PCR reactions: 1) a long-range PCR was performed to amplify the WMS allele on all DNA pools using the KOD FX kit (Toyobo Co., Osaka, Japan); the PCR involved the use of the selective PCR primers, WMS-FP8 and WMS-RP10; the PCR was performed in a 50 μl mixes containing 1×PCR buffer (KOD-Plus-Neo), 1.5 mM MgSO$_4$, 0.2 mM each dNTP, 0.2 μM each primer, 200 ng genomic DNA, 1 U Taq polymerase (KOD-Plus-Neo), and ddH$_2$O; the PCR reactions were carried out under the following conditions: initial denaturation at 94° C. for 2 min, followed by 35 cycles of 98° C. for 10 s, 60° C. for 30 s, and 68° C. 6 min, and a final extension at 68° C. for 10 min; the PCR product was diluted 500 times using ddH$_2$O and then used as the template for the next PCR; 2) the second PCR was performed in a 25 μl mixes containing 1×PCR buffer (1.5 mM MgCl$_2$, 0.2 mM each dNTP; Promega, Madison, USA), 0.2 μM each primers, 2 μl DNA template from the diluted PCR product, 1 U of Taq polymerase (Promega), and ddH$_2$O; the 5922 bp template was split into three fragments for amplification: the first fragment amplified with WMS-FP8 and WMS-RP8, the second fragment amplified with WMS-FP9 and WMS-RP9, and the third fragment amplified with WMS-FP10 and WMS-RP10; PCR reactions were carried out under the following conditions: initial denaturation at 94° C. for 5 min, followed by 35 cycles (94° C. for 30 s, 61° C. for 30 s, 72° C. for 90 s), and a final extension at 72° C. for 10 min A denaturing and re-annealing step is included at the end of the PCR reaction (99° C. for 10 min, 90 cycles of 72° C. for 20 s decreasing 0.3° C. per cycle) to allow the formation of heteroduplexes if a mutation is present in the pool.

After the re-annealing step, the PCR product was digested with celery juice extract (CJE) which was obtained using the protocol described by Till et al. (Till et al., 2006). The amount of CJE for heteroduplex-digestion was optimized as suggested by Uauy et al. (Uauy et al., 2009). The CJE reaction included: 14 μl PCR product, 1 μl CJE, 2 μl 10× digestion buffer (Till et al., 2006) and 3 μl ddH$_2$O for a final volume of 20 μl. The digestion was carried out at 45° C. for 30 min and stopped immediately by adding 5 μl EDTA (75 mM) per sample and mixing thoroughly. Five micro liters of bromophenol blue loading dye (6×) were added and about 24 μl reaction mix was loaded on a 3% polyacrylamide gel (19:1 Acrylamide:bis ratio). Positive pools were identified by detecting cleaved PCR products whose combined size was comparable to the intact PCR product. As for the twofold DNA pools, the presence of a cleaved PCR band indicated there is a point mutation in the PCR template of the selected DNA sample. As for the fourfold DNA pools, a cleaved PCR band indicated one DNA sample of the identified DNA pool must carry a point mutation in the PCR template, which can be identified in the second screen.

The second screen was performed to determine which individual DNA in the fourfold DNA pool actually carries the mutation. Each individual DNA was then pooled twofold with equal amount of genomic DNA from the wild type 'LM15$_{Ms2}$'; these twofold DNA pools were then screened for cleaved products as discovered in the first screen.

To elucidate the base change, a regular PCR was performed on the selected individual DNA; the PCR product was sequenced to reveal the point mutation (FIG. 5). For male-fertile M$_1$ spikes, the identified point mutations were again confirmed in the M$_2$ plants.

TILLING screening revealed 35 mutants among 1200 primary tillers, while there were eight mutants among the 20 male-fertile tillers (FIG. 5). According to primary tillers, the mutation rate of WMS gene is about 2.92%. However, for the 20 male-fertile tillers, there were actually eight tillers carrying detectable mutations, and the 12 tillers likely had no mutations on the WMS gene. Given an independent status between WMS and male fertility (H$_0$ hypothesis), the population mutation rate (2.92%) would be used to calculate expected values for mutation and non-mutation among 20 male-fertile tillers, which are 0.58 and 19.42, respectively. However, the chi-square goodness-of-fit test rejected the null hypothesis ($\chi^2$=97.13, df=1, P=6.49E-23). Therefore, the WMS gene likely determines male sterility in Taigu wheat.

Example 9

Generation of Transgenic Bobwhite Using Biolistic Bombardment

In order to perform genetic complementation, a 10,592-bp genomic fragment (SEQ ID NO: 7) of the WMS gene was cloned from 'LM15$_{Ms2}$' using the KOD FX kit and two specific PCR primers WMS-FP11 and WMS-RP11. After cloning the PCR product to the entry and destination vectors, a plant expression construct (PC976) was prepared, which carried a BAR selection marker (FIG. 4A). BAC clones carrying the WMS gene were obtained in the current invention. It will be convenient to clone the WMS gene (SEQ ID NO: 7) from BAC clones of the current invention. For those who are interested in direct cloning from Taigu wheat, a back-to-back PCR (Vasl et al., 2004) will facilitate the amplification of the full-length WMS gene (SEQ ID NO: 7).

Protocols for the tissue culture and biolistic bombardment of wheat were adapted from previous studies (Weeks et al., 1993; Lv et al., 2014). Immature caryopses from *T. aestivum* cultivar 'Bobwhite' were harvested two weeks after anthesis, sterilized with 70% (v/v) ethanol containing 0.05% (v/v) Tween 20 for 5 min, then with 20% (v/v) Clorox® bleach supplemented with 0.05% (v/v) Tween 20 for 15 min, and washed 3-5 times using sterile distilled water. Immature embryos (ca. 1 mm long) were isolated from the sterilized caryopses, placed with the scutellum facing upward on the dissection media (MS base 4.3 g/L, maltose 40 g/L, thiamine-HCl 0.5 mg/L, L-asparagine 0.15 g/L, 2,4-D 2 mg/L, CuSO$_4$ 0.78 mg/L, Phytagel 2.5 g/L, pH 5.8), and maintained for 4-6 days at 22-23° C. in the dark. Immature embryos were then treated for four hours on the high osmoticum media (MS base 4.3 g/L, maltose 40 g/L, sucrose 171.15 g/L, thiamine-HCl 0.5 mg/L, L-asparagine 0.15 g/L, 2,4-D 2 mg/L, CuSO$_4$ 0.78 mg/L, Phytagel 2.5 g/L, pH 5.8), and subjected to biolistic bombardment. Twenty hours after bombardment, immature embryos were transferred to recovery media (same as the dissection media), maintained for 2 weeks at 22-23° C. in the dark. Embryo-derived calli were moved to the regeneration media (a dissection media supplemented with 0.1 mg/L 6-BA and 3 mg/L bialaphos) and maintained for two weeks in the growth chamber (22-23° C., 16 h light/8 h dark, light intensity of 25 μmol m$^{-2}$ s$^{-1}$). Regenerated shoots (2-3 cm) were transferred to the rooting media (a half-strength dissection media supplemented with 3 mg/L bialaphos), and maintained under the same environmental condition as for regeneration. Vigorous shoots with well-developed roots were established in soil in the greenhouse.

The biolistic bombardment was performed using the PDS-1000/He Particle Delivery System (Bio-Rad Laboratories, USA). To prepare three bombardments, 2 mg of microcarriers (Gold particles of 0.6 μm in diameter; Bio-Rad, USA) were measured into a 1.5 ml microcentrifuge tube, sterilized by mixing with 35 μl pure ethanol, recovered by spinning (12,000 rpm for 5 s) and removing the supernatant, rinsed in 200 μl ice-cold sterile distilled water, and collected by spinning and removing the supernatant. The pre-treated microcarriers were resuspended in 245 μl pre-chilled sterile water containing 20 μg plasmid DNA, and combined with another 250 μl pre-chilled CaCl$_2$ (2.5 M). Where required, solutions in the previous steps were mixed thoroughly by pipetting. The microcarrier suspension was then supplied with 50 µl pre-chilled spermidine solution (1.45%, v/v) and mixed immediately by vortexing in the cold room (4° C.) for 15-20 min. The plasmid-coated microcarriers were recovered by centrifugation (12,000 rpm for 10 s) and followed by removal of the supernatant, and finally resuspended in 36 µl pure ethanol. For each bombardment, 10 µl gold suspension was loaded to the center of a macrocarrier disk (Bio-Rad), air-dried in the laminar flow hood, and placed in the microcarrier launch assembly under the 1100 psi rupture discs. Sixty immature embryos arranged in a 3.5-cm diameter circle were placed 6-cm below the macrocarrier assembly. The PDS-1000/He System was operated according to the manufacturer's instruction. Bombardment conditions were 1,300 psi helium pressure and 25 mm Hg vacuum.

In total, 2742 wheat immature embryos were bombarded with the construct PC976, and 26 plants were regenerated each from an independent embryo (Table 3). In greenhouse, the putative transgenic plants were initially screened by testing their resistance to 0.3% (v/v) Finale® herbicide. At the stem extension stage, all tillers (one leaf perl tiller, 3 cm segment per leaf) were challenged by herbicide painting. Herbicide sensitivity was surveyed five days post painting. The painted region remained green and healthy on herbicide resistant tillers, but wilted on herbicide sensitive tillers. There were only five plants showing herbicide resistance (FIG. 6 and Table 3). At flowering stage, three plants were male sterile, and two of them were herbicide resistant as well (FIG. 6 and Table 3). The presence of the BAR selection marker and the WMS gene were then tested in putative transgenic plants using PCR primers BAR-FP1, BAR-RP1, WMS-FP8 and WMS-RP12. Seven plants were positive for both BAR and WMS genes (Table 3). RT-PCR was used to test the WMS transcription in young spikes, which involved the use of PCR primers WMS-FP6 and WMS-RP6 as for the WMS gene, and Actin-FP1 and Actin-RP1 for the internal control. The WMS cDNA was only detected in three male-sterile transgenic plants (FIG. 6). In conclusion, the introduction of the WMS genomic fragment (SEQ ID NO: 7) and the expression of WMS cDNA (SEQ ID NO: 1) led to male sterility in transgenic wheat. Therefore, the introduction of the WMS genomic fragment (SEQ ID NO: 7) or the WMS cDNA (SEQ ID NO: 1) under an approximate promoter into fertile plants (such as cereal crops, woods, flowers and vegetables) may generate male-sterile transgenic plants. This will greatly advance plant recurrent selection and hybrid seed production.

TABLE 3

Transgenic $T_0$ wheat plants for the WMS genee

| Plant No. | Callus No. | Herbicide Painting | BAR gDNA | WMS gDNA | WMS cDNA | Male Sterility |
|---|---|---|---|---|---|---|
| JZ6-1 | 217 | + | + | + | + | + |
| JZ6-2 | 227 | − | − | − | − | − |
| JZ6-3 | 251 | + | + | + | − | − |
| JZ6-4 | 253 | − | − | − | − | − |
| JZ6-5 | 260 | − | − | − | − | − |
| JZ6-6 | 269 | − | − | − | − | − |
| JZ6-7 | 279 | + | + | + | + | + |
| JZ6-8 | 290 | − | − | − | − | − |
| JZ6-9 | 293 | − | − | − | − | − |
| JZ7-1 | 400 | − | − | − | − | − |
| JZ7-2 | 402 | − | + | + | + | + |
| JZ7-3 | 415 | + | + | + | − | − |
| JZ7-4 | 416 | − | − | − | − | − |
| JZ7-5 | 417 | − | − | − | − | − |
| JZ7-6 | 420 | − | − | − | − | − |
| JZ9-1 | 439 | − | − | − | − | − |
| JZ9-2 | 445 | − | − | − | − | − |
| JZ9-3 | 446 | − | − | − | − | − |
| JZ9-4 | 452 | − | − | − | − | − |
| JZ9-5 | 454 | − | − | − | − | − |
| JZ9-6 | 458 | − | − | − | − | − |
| JZ9-7 | 459 | − | − | − | − | − |
| JZ9-8 | 460 | − | − | − | − | − |
| JZ9-9 | 463 | + | + | + | − | − |
| JZ9-10 | 464 | − | + | + | − | − |
| JZ9-11 | 467 | − | − | − | − | − |

Note: '+' indicated herbicide resistant, BAR gene positive, WMS gene positive, WMS cDNA positive, and male sterile;
'−' indicated herbicide susceptible, BAR gene negative, WMS gene negative, WMS cDNA negative, and male fertile.
Cells with a '+' symbol were highlighted with gray shading. The number of plants positive for each investigated traits were highlighted in the subtotal rows.

Example 10

Generation of Transgenic Brachypodium Using *Agrobacterium*-Mediated Transformation The current invention also validated the WMS gene function in the model plant Brachypodium. The plant expression construct PC976 (FIG. 4A) was delivered into the *Agrobacterium* strain 'AGL1' by electroporation. Transgenic Brachypodium plants were obtained using an *Agrobacterium*-mediated protocol (Bragg et al., 2012).

To prepare bacterium inocula, the *Agrobacterium* AGL1 carrying the construct PC976 was streaked on solid MG/L medium (Tryptone 5 g/L, Yeast extract 2.5 g/L, NaCl 5 g/L, D-Mannitol 5 g/L, MgSO4 0.1 g/L, K2HPO4 0.25 g/L, L-Glutamic acid 1.2 g/L, Agar power 15 g/L, PH 7.2) supplemented with appropriate antibiotics (kanamycin 50 mg/L, carbenicillin 100 mg/L, and rifampicin 40 mg/L), incubated for two days at 28° C. in dark, harvested by scraping *Agrobacterium* colonies off the MG/L medium, and resuspended to an $OD_{600}$ of 0.6 in the liquid CIM.

Immature seeds were collected from *B. distachyon* accession 'Bd21-3' at the seed-filling stage, sterilized in 10% (v/v) Clorox® bleach supplemented with 0.1% (v/v) Triton X-100 for 4 minutes, and rinsed 3 times using sterile water. Immature embryos (0.3-0.7 mm long) were isolated from sterilized seeds, placed with the scutellum facing upwards on the callus initiation media (CIM: LS base 4.43 g/L, GuSO4 0.6 mg/L, Sucrose 30 g/L, 2,4-D 2.5 mg/L, Phytagel 2 g/L, PH 5.8), and incubated at 28° C. in dark. Four weeks later, calli became visible due to the proliferation of the scutellum; only the yellowish embryogenic calli were picked for subculture and *Agrobacterium*-mediated transformation.

Embryogenic calli were infected for 5 minutes by submerging in the fresh *Agrobacterium* inocula that contained 200 µM acetosyringone and 0.1% (w/v) synperonic PE/F68, dried on filter papers to remove free inoculum suspension, and incubated on three layers of filter paper for 3 days at 22° C. in dark. After the co-cultivation, calli were first maintained on the CIM media supplemented with 150 mg/L timentin and 40 mg/L hygromycin for one week at 28° C. in dark, and then subcultured for two more weeks. Vigorous calli were transferred to the regeneration media (Bragg et al., 2012) (LS base 4.43 g/L, GuSO4 0.6 mg/L, maltose 30 g/L, kinetin 0.2 mg/L, Phytagel 2 g/L, PH 5.8) that contained 150 mg/L timentin and 40 mg/L hygromycin, and maintained at 28° C. in LD conditions (16 hours light/8 hour dark, light intensity of 20 μmol m$^{-2}$ s$^{-1}$). When regenerated shoots reached 1-2 cm, they were transferred to the rooting media (Bragg et al., 2012) (MS base with vitamin 4.42 g/L, sucrose 30 g/L, Phytagel 2 g/L, PH 5.8) that contained 150 mg/L timentin, and maintained under the same condition as in the regeneration step. Once the regenerated shoots developed healthy roots (2-3 cm), they were established in soil in the greenhouse.

In total, 100 calli were infected by the *Agrobacterium* strain 'AGL1' with PC976. Eleven plants were recovered from eight independent calli (Table 4). In greenhouse, the putative transgenic plants were initially screened by testing their resistance to 0.3% (v/v) Finale® herbicide. At the three leaf stage (ca. 10 cm high), all tillers (one leaf perl tiller, 1 cm segment per leaf) were challenged by herbicide painting. Herbicide sensitivity was surveyed five days post painting. The painted region remained green and healthy on herbicide resistant tillers, but wilted on herbicide sensitive tillers. There were ten plants showing herbicide resistance (FIG. 7 and Table 4). At flowering stage, ten plants were male sterile, and they were also herbicide resistant (FIG. 7 and Table 4). The presence of the BAR selection marker and the WMS gene were then tested in putative transgenic plants using PCR primers BAR-FP1, BAR-RP1, WMS-FP8 and WMS-RP12. All ten plants were positive for both BAR and WMS genes (Table 4). RT-PCR was used to test the WMS transcription in young spikes, which involved the use of PCR primers WMS-FP6 and WMS-RP6 as for the WMS gene, and Actin-FP1 and Actin-RP1 for the internal control. The WMS cDNA was detected in the ten male-sterile transgenic plants (FIG. 7, Table 4). Taken together, among 11 putative transgenic plants, ten plants were herbicide resistant, positive for both BAR and WMS transgenes, positive for the WMS cDNA, and male-sterile. While there was only one plant being herbicide sensitive, lacking both BAR and WMS transgenes, negative for the WMS cDNA, and be male fertile. Therefore, the genomic fragment of WMS (SEQ ID NO: 7) is potent to induce male sterility in Brachypodium.

Again, the introduction of the WMS genomic fragment (SEQ ID NO: 7) or the WMS cDNA (SEQ ID NO: 1) under an approximate promoter into fertile plants (such as cereal crops, woods, flowers and vegetables) may generate male-sterile transgenic plants. This will greatly advance plant recurrent selection and hybrid seed production.

TABLE 4

Transgenic T$_0$ Brachypodium plants for the WMS genee

| Plant No. | Callus No. | Herbicide Painting | BAR gDNA | WMS gDNA | WMS cDNA | Male Sterility |
|---|---|---|---|---|---|---|
| 22-1 | 22-1 | − | − | − | − | − |
| 22-2 | 22-2 | + | + | + | + | + |
| 22-7 | 22-7 | + | + | + | + | + |
| 22-8 | 22-8 | + | + | + | + | + |
| 22-9 | 22-9 | + | + | + | + | + |
| 22-5A | 22-5 | + | + | + | + | + |
| 22-5B | 22-5 | + | + | + | + | + |
| 22-6A | 22-6 | + | + | + | + | + |
| 22-6B | 22-6 | + | + | + | + | + |
| 22-12A | 22-12 | + | + | + | + | + |
| 22-12B | 22-12 | + | + | + | + | + |

Note: '+' indicated herbicide resistant, BAR gene positive, WMS gene positive, WMS cDNA positive, and male sterile;
'−' indicated herbicide susceptible, BAR gene negative, WMS gene negative, WMS cDNA negative, and male fertile.
Cells with a '+' symbol were highlighted with gray shading. The number of plants positive for each investigated traits were highlighted in the subtotal rows.

Having described the inventions, the following is claimed:

1. A vector comprising the isolated DNA of any one of the following (a) to (g):
   (a) a cDNA comprising the nucleotide sequence of SEQ ID NO: 1, wherein the cDNA encodes a protein which induces wheat male sterility;
   (b) a DNA encoding the amino acid sequence of SEQ ID NO: 2;
   (c) a DNA comprising the nucleotide sequence of SEQ ID NO: 6;
   (d) a DNA encoding a protein which induces wheat male sterility wherein the protein comprises an amino acid sequence with a sequence identity of at least 90% to the entire amino acid sequence of SEQ ID NO: 2;
   (e) a DNA that encodes a protein which induces wheat male sterility and hybridizes under highly stringent conditions to the DNA comprising the nucleotide sequences of SEQ ID NOs: 1 or 6,
   (f) a DNA encoding an antisense RNA that is complementary to the transcription product of the DNA of SEQ ID NOs: 1 or 6, and
   (g) a DNA encoding an RNA that comprises ribozyme activity that specifically cleaves the transcription product of the DNA of SEQ ID NOs: 1 or 6.

2. The vector of claim 1, the isolated DNA being selected from the group consisting of:
   (a) the cDNA comprising the nucleotide sequence of SEQ ID NO: 1;
   (b) the DNA encoding the amino acid sequence of SEQ ID NO: 2;
   (c) the DNA comprising the nucleotide sequence of SEQ ID NO: 6;
   (d) the DNA encoding a protein which induces wheat male sterility wherein the protein comprises an amino acid sequence with a sequence identity of at least 90% to the entire amino acid sequence of SEQ ID NO: 2; and
   (e) the DNA that encodes a protein which induces wheat male sterility and hybridizes under highly stringent conditions to the DNA comprising the nucleotide sequences of SEQ ID NOs: 1 or 6.

3. The isolated DNA of claim 1, wherein the vector further comprises a DNA of any one of the following (a) to (c) that comprises anther-specific promoter activity:
   (a) a DNA comprising the nucleotide sequence of SEQ ID NO: 5;
   (b) a DNA comprising a nucleotide sequence with a sequence identity at least 90% to the nucleotide sequence of SEQ ID NO: 5; and
   (c) a DNA that hybridizes under stringent conditions to the DNA comprising the nucleotide sequence of SEQ ID NO: 5.

4. A plant cell transformed with the DNA of claim 1.

5. The plant cell of claim 4, the vector further comprises a DNA of any one of the following (a) to (c) that comprises anther-specific promoter activity:
   (a) a DNA comprising the nucleotide sequence of SEQ ID NO: 5;
   (b) a DNA comprising a nucleotide sequence with a sequence identity at least 90% to the nucleotide sequence of SEQ ID NO: 5; and
   (c) a DNA that hybridizes under stringent conditions to the DNA comprising the nucleotide sequence of SEQ ID NO: 5.

6. The transformed plant comprising the transformed plant cell of claim 4.

7. A seed, tissue, organ, clone, or offspring of the transformed plant of claim 6.

* * * * *

SEQUENCE LISTING

<160> NUMBER OF SEQ ID NOS: 37

<210> SEQ ID NO 1
<211> LENGTH: 1485
<212> TYPE: DNA
<213> ORGANISM: Artificial Sequence
<220> FEATURE:
<223> OTHER INFORMATION: Synthetic Construct

<400> SEQUENCE: 1

```
cagtacccgc agtggacaca cgcttagctt tagctacgta ggcgcagcag ccggaaacta      60
gctagcaggt cgagaaggcc ggccggaggt agggagatgg cagggcacca cagcccctcg     120
gcggcctcgg cactgcgtga aaaagacacg ctggtgaggt gtctcgtggg atcaggtccc     180
ggcggcggcg ctcatgccgg gaccttcggc gctgtgcggg acttcctcat ccagttccgc     240
gaccaaggaa tcccctgggt ccgcatctac gagtcaaccc cggcttggca gcagcaatcc     300
ggcgggctgc tgatccagga ttgggacgga gacgccgcgg cggagggagc caaggtgttc     360
ttcacgctca tcaccacaag gaggggcggc gccattaaca ggagggcact gggaggcggg     420
acgtggacaa gcaaggccgc gcccaggta ggggacgagg tcgccgtcag cacactgtac     480
ttcaaacggg gcgggtccag cggcagatta ttcaccgcct tggagatcca tctcagaaac     540
gagccccaag ttgctatctg cctgctgcat ccgactaact atctgtatag cattcgggat     600
ttgaggctct acatcgacca gggatggttc ccgggaggaa ctcaagcaaa cctgggcgcg     660
```

-continued

```
gagcaatatc aagatcctga tgttcctgga ttcgtgagtg gttcacgtgc tgattacacc      720
actattctgt tttctagcag tgagactatt tacgaccagc aatcgattca ttcctccggg      780
gctgctctgc cacctcatga tgcatctctg gatgctattt ctcaccacct gttttcagaa      840
aacaactcaa cgccagagtt tggtggacag tattctcatg ctgatgaaat atcaatcctt      900
aatgaatact acaataccttt gatggggacc aactccaact caggattgca tgccttatcc      960
gcagcattct caagttgatg atacgtcatc cccggactac gactacaatc ctttcggaga     1020
gttttgagat tgagagatga catatgagca gtgctgtctg tacatattat ttcttgtaca     1080
gtttctaatt atgaactctt gaataatctt gtcccggtgg acaatgctgt attttatgag     1140
tcttggtagg aatgtatatg tttggtataa atcggtgaa gggtgcatgt agtgtatgac     1200
atcgctttga cggaggaggt gctgattgta cgggactgaa ctgaaggcaa gacagcagca     1260
agcaagcact gacaacgtgt ggattgaata tagctcagac ggctgagagc cggaggtcat     1320
caggcacgat gctcaacgcc ggaggtcaat tgtaattttt atgtaatata atttgcccta     1380
gtgttgcaat atgtacaaat attttagtat tttagcctgt gattcatcgg tccatattaa     1440
tgttattgtg tgaataaatg tttatcaaat cctgcctgtg attta                    1485
```

<210> SEQ ID NO 2
<211> LENGTH: 160
<212> TYPE: PRT
<213> ORGANISM: Artificial Sequence
<220> FEATURE:
<223> OTHER INFORMATION: Synthetic Construct

<400> SEQUENCE: 2

```
Met Ala Gly His His Ser Pro Ser Ala Ala Ser Ala Leu Arg Glu Lys
1               5                   10                  15

Asp Thr Leu Val Arg Cys Leu Val Gly Ser Pro Gly Gly Gly Ala
                20                  25                  30

His Ala Gly Thr Phe Gly Ala Val Arg Asp Phe Leu Ile Gln Phe Arg
            35                  40                  45

Asp Gln Gly Ile Pro Trp Val Arg Ile Tyr Glu Ser Thr Pro Ala Trp
        50                  55                  60

Gln Gln Gln Ser Gly Gly Leu Leu Ile Gln Asp Trp Asp Gly Asp Ala
65                  70                  75                  80

Ala Ala Gly Gly Ala Lys Val Phe Phe Thr Leu Ile Thr Thr Arg Arg
                85                  90                  95

Gly Gly Ala Ile Asn Arg Arg Ala Leu Gly Gly Gly Thr Trp Gly Ser
            100                 105                 110

Lys Ala Ala Pro Arg Val Gly Asp Glu Val Ala Val Ser Thr Leu Tyr
        115                 120                 125

Phe Lys Arg Gly Gly Ser Ser Gly Arg Leu Phe Thr Ala Leu Glu Ile
    130                 135                 140

His Leu Arg Asn Glu Pro Gln Val Ala Ile Cys Leu Leu His Pro Thr
145                 150                 155                 160
```

<210> SEQ ID NO 3
<211> LENGTH: 8657
<212> TYPE: DNA
<213> ORGANISM: Artificial Sequence
<220> FEATURE:
<223> OTHER INFORMATION: Synthetic Construct

<400> SEQUENCE: 3

```
gcggccgcgg gtgaggcttt gccaaggcat caatggatcc cgaggacatg ctgctcgcgt       60
```

```
cggtcctccg ccgctccctg acgatgtcgg agacagatgc gcggcggtgg gtggggcatt    120
ggcgaggcgc tggtggatct ggaggacatg ctcctcgtgt cggtcctccg ccgctccctg    180
acgacggtag agacggatgc gcggtgatgg gtgaggcgtt ggggaggctc cggtggatcc    240
cgagaacacc ctcctcgcat cggtcccccg ctgcttgcta cgacggcgg agagggatgc     300 gcggcggcgg gtgaggcgtt ggagaggcgc tggtggatcc agaggacacg ctccttgtgc    360
ggatcctccg ccgctccctg atggcagcga gagggatgc gcggcggcgg gtgaggcgtt     420
ggggaggcgc cggtggatcc cgaggacacg ctcctcgcgt cggtctccgc cgctccctga    480
cgacgacgga gacggatgca cggcggcggg tgaggcgttg gcgaggcgtc ggtggatccc    540
gaagacacgc tcctcgcgtt ggtcctccgc tgctcgctga caatggcaga gagggatgcg    600
tggcggcggg tgaggcgttg gagaggcgtc gatggatccg gaggacacgc tcctcgtgtc    660
aatcctccgc cggtccctga tgacggcgga gaggggtgcg cggcggcggg tgaggcattg    720
gggaggcgct ggtggatccc gaggacatgc tcctcgcgtc ggtcctccgc tgcccctga    780 cgaaggcgaa gacggatgcg aggcgccggg tgaggcattg tcgaggcgtc ggtggatccc    840
gaggacacgc tcgtcaagtc agtcctccgc cgctccctgt cgacggtgga gacggtttca    900
tggcgatggg tgaggcgtcg gcaaacgcgt gcactggtgg atccttagga cacgctcgtt    960
acgtcggtcc tccgccgctc cctgacgatg gtggagactg atgcacggcg gctctggcat   1020
cgagctgtcc gagcacgagg caatggtgca agttgcggcg aaggcgaaca ccgaggagta   1080
ggagcgcttg ctccagggc tggccgcgca gatctcctcg gacggccatg accctccgac    1140
ggccaaggcc agcgcacgac cccaaacgga cgtccggttt ggcctgcttt cgtctgtttg   1200
cggcggcaat gggttcgccc atgtctgctt gggtccgttg ggttgtcgat atgcccaacg   1260
cacggccgca ccccaaatca tgtccagggt ggacgtgatt aaaaaaacac aaaaactaaa   1320
atgaaatgcc aaaaaatta aataaatgca agcataaaaa tataaaacat aaattaacca    1380
tcacggccac aaaacggccc agttccatgg ttcacataga cataattaac ataaaaacaa   1440
aataaaaccg ccgcccacgc gctcctgccg tgcccgtcgc cgtcttctca gtggccgccg   1500
ttgtcgtcgt tgtcgctgac gaggtcgacg tagtccggcg gcgtccagag gtgggacggc   1560
ggtgcgtggt acacggggc gggctggaag gcgggaggtg cctacacctc ctcctcctgt    1620
ggcgacgcct cccgctccgg tgaccatggc gttgtgggc accagtccac tgctagccca    1680
ccaggcccgg gtggaacaca gccacgggct cctcctccat cacctcctcc gtcctcacca   1740
tctccagctc ggggatggcg acgtcgccgg ccgcagagag ggccatcatc tcttcgaggc   1800
cctcccattg gcgctcatcg tgcgtcttca tggagtcctc catgacacgt gcatgagcc    1860 gggcctcctc ctccgctgtc atgcgaggag gtggtggtgg cagcggagat ggtgaaggcg   1920
acggcgtggg cgtgaggccg cgcacccgcg tacgcctgcg cacctgggga gcagccgctg   1980
cgcgctctcg acgtggccgt gcggccccg acaaggtgcc ggcgaagaaa aaggcgcgac    2040
gcgtgtcgtg ctcgtcccga aaccacgtgt cccacaggtc ggagtcgggg cgtaccgag    2100 ggtcgtagta caggtcgtcc ggcaggaggc ggcggcggca ctggatctcc tcgcggcgcg   2160
cacggccgct cgtcgggacc ggcgggatcg gcacccggtt ggcggagaga tgccagttat   2220
tggggaggtg cacgtcgctc catgggagcg gcgtcctcgt ctcccaataa cgccggcata   2280
catccgcgtg gatgtactgc tggtcgcgct tgccgccggc cgtagggccg atggtgaatg   2340
gggcaggcgt gggggctcga tgcggtggtg atgcgggctc ctctttcatg gagccgcggc   2400
```

```
ggcggcccga ggacgagcca gcctcgtggt cgcgcttccc cttgcgaccg gtgttccaga    2460
accccatggc tgcgaggcgg ccggccgacg agatcgagga cggggagagg gagagctagg    2520
gtttggggtg tgtcgggttt cgaggaggca gcacgggctg gagtggagag tgtggacgac    2580
gaccggtcca cggtttccca tttaagaagg acggtgactg tttgctggac ggatgacagg    2640
tggggccgac cgcgcgtgcg cattaatgtt ggctggtggg aggtaggtgt ccgcctgcca    2700
cgcggcctcg aagcggacga gcgacgcgtc cgtttgctgt ccgccgcgac ccaaatccgg    2760
cacatgtttg cgctcgaaat gggtcggcct ggacacaaaa cggaccagat gggctcaggc    2820
cgtcgcgcgc tgggccgtgg gatttgttcg ttttgtccca aatggacggg gccggacggg    2880
atggggtcgc gcgcaagggc gagagcagaa ccatcgaccg caagcggtga ttttgtgcgc    2940
accttctgcc ataggtgtag ctcgtcgact gccaagtata tcactgtctc gcgatttgag    3000
catagagtca atcgattttc ctggccaatg gcgtcaaggg gagagatttg gtcaatgggc    3060
ggaagtcgca gacccatgta catgtgcacg ggtgggtgcc ttatgtgatt tgacctctct    3120
acggcgcacc agtactggac ggctcgtttc ttattctaaa cacagatact agtgtgcacc    3180
ctgttgatat ttgatatttg agatttgaga gtgcggcacc cgactgcaca gtccacatgc    3240
atgcagctgg ctctttctct tgacttgaca cgctctcgct tctcccgatt cctgcccgcg    3300
ccggcgtctc cacccgactt gatcgacatc ggcatcggca tcggcctcgg catcggcccc    3360
tcgacgacgc tcagtatata agcgatcggg ctggtggagc tgcttgcagt acccgcagtg    3420
gacacacgct tagctttagc tacgtaggcg cagcagccgg aaactagcta gcaggtcgag    3480
aaggccggcc ggaggtaggg agatggcagg gcaccacagc ccctcggcgg cctcggcact    3540
gcgtgaaaaa gacacgctgg tggggtgtct cgtgggatca ggtcccggcg gcggcgctca    3600
tgccgggacc ttcgacgctg tgcgggactt cctcatccag ttccgcgacc aaggaatccc    3660
ctgggtccgc atctacgagt caaccccggc ttggcagcag caatgtgagt aatctaatct    3720
ccactgttga ttgatctgca taatgctact cattctcact atcgcctggc cggcctcgtg    3780
atcaacatga atgcgcgcgt atgttatgca gccggcgggc tgctgatcca ggattgggac    3840
ggagacgccg cggcggaggg agccaaggtg ttcttcacgc tcatcaccac aaggagggc    3900 ggcgccatta acaggagggc actgggaggc gggacgtgga caagcaaggc cgcgcccagg    3960
gtaggggacg aggtcgccgt cagcacactg tacttcaaac ggggcgggtc cagcggcaga    4020
ttattcaccg ccttggagat ccatctcaga aacgaggtat gctgtgcttg ctccatccat    4080
cgcatttttt ttgttttgtt ttaaatttgc ttatgcgact atatattatc atggttgttg    4140
cccacgttgt tcaaagattt gcgcccctgc ttgaaactgc tggtatatat gaaccctttt    4200
cttaagcttc ggtgtaggac tacggctccg ttcgtttttt ctccttctct cgccaaaaca    4260
aattccatct caccgatctc ttctcccgtc ggcgacgaac cctagctacg tacctagcca    4320
gctcggatca gtccgcttcc cttcaaaaaa agaaaaataa aaatccatct cactgaagtt    4380
gcatttcaac attgctgttc cgtacatcta aacttatata tgaaccccctt tgtcaagcta    4440 aatttcaacg gcaagtgtgg tcaactatct catgttgact tgatgagcat gtgccggccc    4500
gatcgatgta gtagaaggag aagagctagc gaacaagaca aaaaatcagg agaatcatga    4560
cgacatgatc aacagtagat tagtccttt tattatatag gatgatccca attcgtttgt    4620
tctctagcta gagcaatata atactatagg atcagtactt tttaggggca caccaccata    4680
aggttagtcc taagttgacc ttcttctgct gcccttaaac ctcgtcgtca tagcccagct    4740
agtaaaccct ctccctcggt ctgtttctta cgagcccaag cagcccgttc cgtttcctca    4800
```

```
cgagcccaag cccagcttgt aaacccttcc gtccccgcc tcgtctcgtc cagtccagac    4860
ccctcttctc ttctagtcaa cggtcgccgg cggcggcggc gccaagtcat ccaagacaca    4920
gagcgctcag ccgcagcccc gaaccctaga aatcaagcga acgcggcggc gaggttccgg    4980
ttggggagat gcacttcttt tttcagcaag tcagtgaaaa ttatatgttg atctttcgtg    5040
tttgtttctg tttttctagc cccaagttgc tatctgcctg ctgcatccga ctaaatatct    5100
gtatagcatt cgggatttga ggctctacat cggccaggta aatattttct atttccagtt    5160
ttggttttca cccgtgggcg ctactttcaa tgttcggtct acaagccaat tagctgattc    5220
agttgctgaa cgataaaaca agaccgattc cactatgcat gttttgctac aaatgaatga    5280
gcccaacaac attactatga ggttactctc ctctttcagg gatggttccc gggaggaact    5340
caagcaaacc tgggcgcgga gcaatatcaa ggtattcata agtcatgatt gatccccaat    5400
gccttcgaca gtttaactga aacaggcacc atctgtactt tgttgaaac atagtgatct    5460 ttgatctggg tacatagata gccctgattt catatatcta cgtccttaca ttagtcatgg    5520
aaatatgaaa acgaggtaga ttgatctgtt attttatcct attacttagc atttttgtac    5580
ttgtacatct tatttcggca gataaattta aaaccccaca gctgatatat atattatcct    5640
caatttatac actatttgat gaattgataa ggtaagaact cataagtcga gaactctaga    5700 tataccag gacgtctac tatcagaaca catgattgaa cataaatcaa tcactgcaga    5760
atgatatttg aactaagcgt ttatcagtca taagatagac atattgttgt tttccaatat    5820
atattgtgga atttaatctg ggctatatgt aatagctcca attctctgcg ctgtggcata    5880
ttaaatcgca ttggtcttac actggcagaa gttttacatg ctaccttgct tgcagatcct    5940
gatgtttctg gattcgtgag tggttcacgt gctgattaca ccactattct gttttctagc    6000
agtgaggtaa ttaagctttc catgcacaaa ctagaacaag ttaccaccaa atttagattt    6060
cttgtacaac ccctatgctt atctaaatgt gacaactcaa gttctattat ctctagtaag    6120
aagacataga agatgtttta ttaagtcaat ttctgttctt acgtactccc tctgtcccac    6180
aatgtaacac gtttaacgtc ttgcattgtg ggacggaggg agagaacttg tcatttgctt    6240
actggtattg gagttagact ggtatactta attgggaaat cattttgaaa actaaggcat    6300
cgagtccttc actgttctgg gtgtactgag gtaaacaaca tgcacttcgg atgagatggg    6360
agaattaggc tattagcact caggattagc ctacagatag gttttatgca cagcacaacc    6420
tatatatgag atattttaca taccgtatga tacctgtaaa cattgataag tggtatatct    6480
caacaccatg cataattaat tgcaatacta cagaatgtac tagacaattc tggaccctcc    6540
gatttggatc tggcggccga tatagtcctt ctcccatgtt gttttttgtta tatagaacac    6600 ttgtttggag tgaatttagc gtacattatc tggaacttca gttttgtct gttgataatt    6660 ggcttacagc tgcatttcag aacataacaa tgtgagtttg aacagactat ttacgaccag    6720
caatcgattc attcctccgg ggctgctctg ccacctcatg atgcatctct ggatgctatt    6780
tctcaccacc tgttttcaga aaacaactca acgccagagg tactatacaa ttacattcat    6840
cctcggtctt gttgcatcac cacatttta tttattttc agttgatcta cgatttccgt    6900
gttttagttg ccacatatat tgcaagtaaa ctgatcttat atttccttt gcttgcagtt    6960 tggtggacag tattctcatg ctgatgaaat atcaatcctt actgaatact acaataccttt    7020 gatgggacc aactccaact caggatagca tggtacgctt ctttgctgtt gaataagtg    7080 gtaacgtagg accaacaaca ttgcttttc aaaattttcaa gtagtttgga cctgaataca    7140
```

```
agtaagaaaa agatgatcct tcagtgttct gttctctttg gctaaaatga caagtaattt    7200
gcacctttct cctgttttgg aatattattg ttacacactt gaatccatag ggttttatag    7260
caactttgga ggattttatt ccgttggatt gctcatggat acccttgatc aaagtaatga    7320
ccatcataat ttctatgaat tgtattttcc tacacccctt ttcccgtagg attctacaca    7380
ccaaagaatt ttgccgttgt tgtcaagtgg tgttcacctg cacgtgctac cttcaatgtt    7440
tgttccagaa gccaattaac tacattgatt cgtatgagca cacagtacta agcctactaa    7500 taggttttc cacagcacta ccattgttaa tatatatgta catacgagat attgtgcata     7560
ctgttataag gttactgtaa atatcgatta gtgatatgtc cttgcaaaac aagaagagaa    7620
gtttgtaggg ccgtgtttta gtcccacaca tatgttgaaa tcgagctgac cttatgttcc    7680
cttttttttt tgcagcctta tccgcagcat tctcaagttg atgatacgtc atccccggac    7740
tacgactaca atcctttcgg agagttttga gattgagaga tgacatatga gcagtgctgt    7800
ctgtacatat tatttcttgt acagtttcta attatgaact cttgaataat cttgtcccgg    7860
tggacaatgc tgtattttat gagtcttggt aggaatgtat gtgtttggta taaaatcggt    7920
gaagggtgca tgtagtgtat gacatcgctt tgacggagga ggtgctgatt gtacgggact    7980
gaactgaagg caagacagca gcaagcaagc actgacaaag tatggattga atatagctca    8040
gatggctgag agccggaggt catcaggcac gatgctcaac gccggaggtc aattgtaatt    8100
tttatgtaat ataatttgcc ctagtgttgc aatatgtaca aatattttag tattttagca    8160
tgtgattcat cggtccatat taatgttatt gtgtgaataa atgtttatca aatcctgcct    8220
gtgatttatc tgcccatgtt ttaggatttt attttgtaat cacttattga cttagcaaag    8280
aagatgtaag tttattcggt ataagttaat aaaaagtgaa acagttaagg cgggttttca    8340
aggaatgata tacttagtaa aagaatggaa ggttggacaa agcattgcgc ctggcagaaa    8400
aaggaacgat ttgtttttg aactagtata gagatttcac ttgagctgag ggccattaca    8460
caccaactgt atatgtttca gctctgcaac agcatcgtcg tgatggtcgt catttgatct    8520
cctacctcga ccgagtagct catcaaccga gttattttgc agtacatcaa acaaatatgg    8580
gtcgtccatt cccatcatct gatagtctag atccatccat actaccgtat tttagtagca    8640
catggacacg gagatcg                                                   8657
```

<210> SEQ ID NO 4
<211> LENGTH: 10592
<212> TYPE: DNA
<213> ORGANISM: Artificial Sequence
<220> FEATURE:
<223> OTHER INFORMATION: Synthetic Construct

<400> SEQUENCE: 4

```
gcggccgcgg gtgaggcttt gccaaggcat caatggatcc cgaggacatg ctgctcgcgt      60
cggtcctccg ccgctccctg acgatgtcgc agacagatgc gcggcggtgg gtggggcatt     120
ggcgaggcgc tggtggatct ggaggacatg ctcctcgtgt cggtcctccg ccgctccctg     180
acgacggtag agacggatgc gcggtgatgg gtgaggcgtt ggggaggctc cggtggatcc     240
cgagaacacc ctcctcgcat cggtcccccg ctgcttgcta acgacggcgg agagggatgc     300
gcggcggcgg gtgaggcgtt ggagaggcgc tggtggatcc agaggacacg ctccttgtgc     360
ggatcctccg ccgctccctg atggcagcga gagggatgc gcggcggcgg gtgaggcgtt      420
ggggaggcgc cggtggatcc cgaggacacg ctcctcgcgt cggtctccgc cgctccctga     480
cgacgacgga gacggatgca cggcggcggg tgaggcgttg gcgaggcgtc ggtggatccc     540
```

```
gaagacacgc tcctcgcgtt ggtcctccgc tgctcgctga caatggcaga gagggatgcg    600
tggcggcggg tgaggcgttg gagaggcgtc gatggatccg gaggacacgc tcctcgtgtc    660
aatcctccgc cggtccctga tgacggcgga gaggggtgcg cggcggcggg tgaggcattg    720
gggaggcgct ggtggatccc gaggacatgc tcctcgcgtc ggtcctccgc tgcccctga    780 cgaaggcgaa gacggatgcg aggcgccggg tgaggcattg tcgaggcgtc ggtggatccc    840
gaggacacgc tcgtcaagtc agtcctccgc cgctccctgt cgacggtgga gacggtttca    900
tggcgatggg tgaggcgtcg gcaaacgcgt gcactggtgg atccttagga cacgctcgtt    960
acgtcggtcc tccgccgctc cctgacgatg gtggagactg atgcacggcg gctctggcat    1020
cgagctgtcc gagcacgagg caatggtgca agttgcggcg aaggcgaaca ccgaggagta    1080
ggagcgcttg ctccagggcc tggccgcgca gatctcctcg gacggccatg accctccgac    1140
ggccaaggcc agcgcacgac cccaaacgga cgtccggttt ggcctgcttt cgtctgtttg    1200
cggcggcaat gggttcgccc atgtctgctt ggtccgttg ggttgtcgat atgcccaacg    1260
cacggccgca ccccaaatca tgtccagggt ggacgtgatt aaaaaaacac aaaaactaaa    1320
atgaaatgcc aaaaaatta aataaatgca agcataaaaa tataaaacat aaattaacca    1380
tcacggccac aaaacggccc agttccatgg ttcacataga cataattaac ataaaaacaa    1440
aataaaaccg ccgcccacgc gctcctgccg tgcccgtcgc cgtcttctca gtggccgccg    1500
ttgtcgtcgt tgtcgctgac gaggtcgacg tagtccggcg gcgtccagag gtgggacggc    1560
ggtgcgtggt acacggggc gggctggaag gcgggaggtg cctacacctc ctcctcctgt    1620
ggcgacgcct cccgctccgg tgaccatggc gttgtggggc accagtccac tgctagccca    1680
ccaggcccgg gtggaacaca gccacgggct cctcctccat cacctcctcc gtcctcacca    1740
tctccagctc ggggatggcg acgtcgccgg ccgcagagag ggccatcatc tcttcgaggc    1800
cctcccattg gcgctcatcg tgcgtcttca tggagtcctc catgacacgt tgcatgagcc    1860
gggcctcctc ctccgctgtc atgcgaggag gtggtggtgg cagcggagat ggtgaaggcg    1920
acggcgtggg cgtgaggccg cgcacccgcg tacgcctgcg cacctgggga gcagccgctg    1980
cgcgctctcg acgtggccgt cgcggccccg acaaggtgcc ggcgaagaaa aaggcgcgac    2040
gcgtgtcgtg ctcgtcccga aaccacgtgt cccacaggtc ggagtcgggg gcgtaccgag    2100
ggtcgtagta caggtcgtcc ggcaggaggc ggcggcggca ctggatctcc tcgcggcgcg    2160
cacggccgct cgtcgggacc ggcgggatcg gcacccggtt ggcggagaga tgccagttat    2220
tggggaggtg cacgtcgctc catgggagcg gcgtcctcgt ctcccaataa cgccggcata    2280
catccgcgtg gatgtactgc tggtcgcgct tgccgccggc cgtagggccg atggtgaatg    2340
gggcaggcgt ggggctcga tgcggtggtg atgcgggctc ctctttcatg gagccgcggc    2400
ggcggcccga ggacaagcca gcctcgtggt cgcgcttccc cttgcgaccg gtgttccaga    2460
accccatggc tgcgaggcgg ccggccgacg agatcgagga cggggagagg gagagctagg    2520
gtttggggtg tgtcgggttt cgaggaggca gcacgggctg gagtggggag tgtggacgac    2580
gaccggtcca cggtttccca tttaagaagg acgcgactg tttgctggac ggatgacagg    2640
tggggccgac cgcgcgtgtg cattaatgtt ggctggtggg aggtaggtgg ccgcctgcta    2700
cgcggcctcg aggcggacga gcgacgcgtc cgtttgctgt ccgccgcgac ccaaatccgg    2760
cacatgtttg cgctcgaaat ggatcggccc ggacacaaaa cggaccagat aggttcaggc    2820
cgtcgcgcgc tgggcgtggg atttgttctt ttgtcccaaa tggacggggc cggacgggat    2880
```

-continued

| | |
|---|---|
| ggggtcgcgc gcaagggcga gagcagaacc atcgaccgca agcggtgatt ttctgcgcac | 2940 |
| cttctgccat aggtgtagct cgtcgaccgc caagtatatc actgtctcgc gatttgagca | 3000 |
| tagagtcaat cgattttcct ggccaatggc gtcaagggga gagatttggt caaatgggcg | 3060 |
| gaagtcgcag acccatgtat atgtgcacgg gtgggtgggt gccttagggc atttacaacg | 3120 |
| caaggcgcta aggcgggcgc cagggtcagg atcctagtcg tttggcttag ttcccgtcca | 3180 |
| aatttgagaa ttgagctggc atcgatgcca tataagtcgt cgggcgtcgg gcgctaactc | 3240 |
| agttttctgt ctatttatg tgtgtagcgc tcatacgtgg ctctcagcgt tggaagaggg | 3300 |
| actcttagcc caggcgctag gaagaaaata ctattttatt tccagtcaag tgcctgatta | 3360 |
| ggcgccctcc attggagatg cccttatgtg cctctctacg ccgcagcagc cggaaactac | 3420 |
| ggcgcaccag tactgacgg ctcgtttctt attctaaaca cagatactag tgttgttgcc | 3480 |
| gccagtccct cgccgccgga gctctctctc tctctctccc tcgcacaaac atagaagaaa | 3540 |
| gaaggaagag gagcgatgca gtggacacaa caagctttac gcggtgcacg tacgctgccg | 3600 |
| gccgcacgaa cagccgatcg ttttcattcc tgagctcgaa ctcagccacc ggacaacaac | 3660 |
| gagtacacag agggccttct atacccaagc tacacacatc aggctagcta ccacacgcaa | 3720 |
| gcacgcatgc atccactgca gcgaaagcta actacatgca cgcatgcagc ccacgacccg | 3780 |
| gctgcatgac gcccgcgcct gccgagtcca cgatccgcac ggcgtgacca actaactgca | 3840 |
| tgcaactaga cggagcgccc acgcaacgcc cgccccgcgc tcctcagctc ccgcgcccgc | 3900 |
| cgcgcacgca cgccaacggg atacgactgg ttccagcgcc tggcgcggtc acacctcgcg | 3960 |
| cgtccgtcta accaacacac acacacatga ccccgccgcg cacccgccgc gcccgacacg | 4020 |
| cccggcgcaa tcgcggtggc ttatgcccaa cactcacccc ccttagccac gaattacagc | 4080 |
| aggtgagttc atcatcgtcg atgtcgccat ggccgtcgca tcgcaccgct gcggcctccg | 4140 |
| ccatgccgtc gacgtcgttg tagccgccgc cgtcctgacg tcgctgccac acctgccacc | 4200 |
| gtgccgccgt gcccttcgcg tgcactcccc gcgctcccgg cccgcgctcc cgcgcgcacg | 4260 |
| tacgctatct gcgcaactag gtccagtgtc tcgacgcggt ccactcccac ggtcccgacg | 4320 |
| cgtctggtgc gcacccataa cacgcaccgg tcgcgcccgg ctcgccaccg cgtcttattg | 4380 |
| ccctgcactg ccgtgccgtc aaccgtagcg cagcgcctcc acggtcgtcg cgccgagccg | 4440 |
| ccgcggcctc tgcgacacca cgcaggtcct ccgcgacctc ctcgtctccg cgaccgccac | 4500 |
| tgctcgccgc gcgcacggca tcacgccaca ccgccgtgga ctcgccgcgc gttgccgacg | 4560 |
| ccacgcgctc gccgcacgcc cggcatcacg ccacaccgcc gtggactcgc gcgcgttgc | 4620 |
| cgagatcttc atgtccgccg cgcgccacgg ccgcccccg aacctgtggc tctgatacca | 4680 |
| aatgttgttg ccgccagtcc ctcgccgccg gagctctctc tctctctctc cctcgcacaa | 4740 |
| acatagaaga aagaaggaag aggagcgatg cagtggacac aacaagcttt acgcggtgca | 4800 |
| cgtacgctgc cggccgcacg aacagccgat cgttttcatt cctgagctcg aactcagcca | 4860 |
| ccggacaaca acgagtacac agagggcctt ctatacccaa gctacacaca tcaggctagc | 4920 |
| taccacacgc aagcacgcat gcatccactg cagcgaaagc taactacatg cacgcatgca | 4980 |
| gcccacgacc cggctgcatg acgcccgcgc ctgccgagtc cacgatccgc acggcgtgac | 5040 |
| caactaactg catgcaacta cggagcgc ccacgcaacg cccgccccgc gctcctcagc | 5100 |
| tcccgcgccc gccgcgcacg cacgccaacg ggatacgact ggttccagcg cctggcgcgg | 5160 |
| tcacacctcg cgcgtccgtc taaccaacac acacacacat gaccccgccg cgcacccgcc | 5220 |
| gcgcccgaca cgcccggcgc aatcgcggtg gcttatgccc aacaactagt gtgcacctcg | 5280 |

```
ttgagagtgc ggcacccgac tgcacagtgc acatgcatgc agctggctct ttctcttgac    5340
ttgacacgct ctcgcttctc ccgattcctg cccgcgccgg cgtctccacc cgacttgatc    5400
gacatcggca tcggcatcgg cctcggcatc ggcccctcga cgacgctcag tatataagcg    5460
atcgggctgg tggagctgct tgcagtaccc gcagtggaca cacgcttagc tttagctacg    5520
taggcgcagc agccggaaac tagctagcag gtcgagaagg ccggccggag gtagggagat    5580
ggcagggcac cacagcccct cggcggcctc ggcactgcgt gaaaaagaca cgctggtgag    5640
gtgtctcgtg ggatcaggtc ccggcggcgg cgctcatgcc gggaccttcg gcgctgtgcg    5700
ggacttcctc atccagttcc gcgaccaagg aatcccctgg gtccgcatct acgagtcaac    5760
cccggcttgg cagcagcaat gtgagtaatc taatctccac tgttgattga tctgcataat    5820
gctactcatt ctcactatcg cctggccggc ctcgtgatca acatgaatgc gcgcgtatgt    5880
tatgcagccg gcgggctgct gatccaggat tgggacggag acgccgcggc ggagggagcc    5940
aaggtgttct tcacgctcat caccacaagg aggggcggcg ccattaacag gagggcactg    6000
ggaggcggga cgtggacaag caaggccgcg cccagggtag gggacgaggt cgccgtcagc    6060
acactgtact tcaaacgggg cgggtccagc ggcagattat tcaccgcctt ggagatccat    6120
ctcagaaacg aggtatgctg tgcttgctcc atccatcgca tttttttttgt tttgttttaa    6180 atttgcttat gcgactatat attatcatgg ttgttgccca cgttgttcaa agatttgcgc    6240
ccctgcttga aactgctggt atatatgaac ccttttctta agcttcggtg taggactacg    6300
gctccgttcg ttttttctcc ttctctcgcc aaaacaaatt ccatctcacc gatctcttct    6360
ccgtcggcga cgaaccctag ctcggatcag tccgcttccc ttcaaaaaaa agaaaaataa    6420
aaatccatct cactgaagtt gcatttcaac attgctgttc cgtacatcta aacttacata    6480
tgacgacatg atcaacagta gattagtcct ttttattata tataggatga tcccaattcg    6540
tttgttctct agctagagca atataatact ataggatcag tacttttttag gggcacacca    6600 ccataaggtt agtcctaagt tgaccttctt ctgctgccct taaacctcgt cgtcatagcc    6660
cagctagtaa accctcgccc tcggtctgtt tcttacgagc ccaagcagcc cgttccgttt    6720
cctcacgagc ccaagcccag cttgtaaacc cttccgtccc ccgcctcgtc tcgtccagtc    6780
cagacccctc ttctcttcta gtcaacggtc gccggcggcg gcggcgccaa gtcatccaag    6840
acagagagcg ctcagccgca gccccgaacc ctagaaatca agcgaacgcg gcggcgaggt    6900
tccggttggg gagatgcact tcttttttca gcaagtcagt gaaaattata tgttgatctt    6960 tcgtgttttgt ttctgttttt ctagccccaa gttgctatct gcctgctgca tccgactaac    7020
tatctgtata gcattcggga tttgaggctc tacatcgacc aggtaaatat tttctatttc    7080
cagttttggt tttcacccgt gggcgctact ttcaatgttc ggtctacaag ccaattagct    7140
actgtagatt gattcagttg ctgaacgata aaacaagacc gattccacta tgcatgtttt    7200
gctacaaatg aatgagccca acaacattac tatgaggtta ctctcctctt tcagggatgg    7260
ttcccgggag gaactcaagc aaacctgggc gcggagcaat atcaaggtat tcataagtca    7320
tgattgatcc ccaatgcctt cgacagttta actgaaacag gcaccatctg tacttttgtt    7380
gaaacatagt gatctttgat ctgggtacat agatagccct gatttcatat atctacgtcc    7440
ttacattagt catggaaata tgaaaacgag gtagattgat ctgttatttt atcctattac    7500
ttagcatttt tgtacttgta catcttattt cggcagataa atttaaaacc ccacagctga    7560
tatatatatt atcctcaatt tatacactat ttgatgaatt gataaggtaa gaactcataa    7620
```

```
gtcgagaact ctagatatat accagggacg tctactatca gaacacatga ttgaacataa    7680
atcaatcact gcagaatgat atttgaacta agcgtttatc agtcataaga tagacatatt    7740
gttgttttcc aatatatatt gtggaattta atctgggcta tatgtaatag ctccaattct    7800
ctgcgctgtg gcatattaaa tcgcattggt cttacactgg cagaagttttt acatgctacc    7860 ttgcttgcag atcctgatgt tcctggattc gtgagtggtt cacgtgctga ttacaccact    7920
attctgtttt ctagcagtga ggtaattaag ctttccatgc acaaactaga acaagttacc    7980
accaaattta gatttcttgt acaacccta tgcttatcta aatgtgacaa ctcaagttct    8040
attatctcta gtaagaagac atagaagatg ttttattaag tcaatttctg ttcttacgta    8100
ctccctctgt cccacaatgt aacacgttta acgtcttgca ttgtgggacg gagggagaga    8160
acttgtcatt tgcttactgg tattggagtt agactggtat acttaattgg gaaatcattt    8220
tgaaaactaa ggcatcgagt ccttcactgt tctgggtgta ctgaggtaaa caacatgcac    8280
ttcggatgag atgggagaat taggctatta gcactcagga ttagcctaca gataggtttt    8340
atgcacagca caacctatat atgagatatt ttacataccg tatgatacct gtaaacattg    8400
ataagtggta tatctcaaca ccatgcataa ttaattgcaa tactacagaa tgtactagac    8460
aattctggac cctccgattt ggatctggcg gccgatatag tccttctccc atgttgtttt    8520
tgttatatag aacacttgtt tggagtgaat ttagcgtaca ttatctggaa cttcagtttt    8580
tgtctgttga taattggctt acagctgcat ttcagaacat aacaatgtga gtttgaacag    8640
actatttacg accagcaatc gattcattcc tccgggctg ctctgccacc tcatgatgca    8700
tctctggatg ctatttctca ccacctgttt tcagaaaaca actcaacgcc agaggtacta    8760
tacaattaca ttcatcctcg gtcttgttgc atcaccacat tttatttat ttttcagttg    8820 atctacgatt tccgtgtttt agttgccaca tatattgcaa gtaaactgat cttatatttc    8880
cttttgcttg cagtttggtg gacagtattc tcatgctgat gaaatatcaa tccttaatga    8940
atactacaat accttgatgg ggaccaactc caactcagga ttgcatggta cgcttctttg    9000
ctgttgaaat aagtggtaac gtaggaccaa caacattgct ttttcaaaat ttcaagtagt    9060
ttggacctga atacaagtaa gaaaaagatg atccttcagt gttctgttct ctttggctaa    9120
aatgacaagt aatttgcacc tttctcctgt tttggaatat tattgttaca cacttgaatc    9180
catagggttt tatagcaact ttggaggatt ttattccgtt ggattgctca tggatacct   9240 tgatcaaagt aatgaccatc ataatttcta tgaattgtat tttcctacac cccttttccc    9300
gtaggattct acacaccaaa gaattttgcc gttgttgtca agtggtgttc acctgcacgt    9360
gctaccttca atgtttgttc cagaagccaa ttaactacat tgattcgtat gagcacacag    9420
tactaagcct actaataggt ttttccacag cactaccatt gttaatatat atgtacatat    9480
gagatattgt gcatactgtt ataaggttac tgtaaatatc gattagtgat atgtccttgc    9540
aaaacaagaa gagaagtttg tagggccgtg ttttagtccc acacatatgt tgaaatcgag    9600
ctgaccttat gttcccgttt tttttgcag ccttatccgc agcattctca agttgatgat    9660
acgtcatccc cggactacga ctacaatcct ttcggagagt tttgagattg agagatgaca    9720
tatgagcagt gctgtctgta catattattt cttgtacagt ttctaattat gaactcttga    9780
ataatcttgt cccggtggac aatgctgtat tttatgagtc ttggtaggaa tgtatatgtt    9840
tggtataaaa tcggtgaagg gtgcatgtag tgtatgacat cgctttgacg gaggaggtgc    9900
tgattgtacg ggactgaact gaaggcaaga cagcagcaag caagcactga caacgtgtgg    9960
attgaatata gctcagacgg ctgagagccg gaggtcatca ggcacgatgc tcaacgccgg   10020
```

```
aggtcaattg taattttttat gtaatataat ttgccctagt gttgcaatat gtacaaatat    10080
tttagtattt tagcctgtga ttcatcggtc catattaatg ttattgtgtg aataaatgtt    10140
tatcaaatcc tgcctgtgat ttatctgccc atgttttagg attttatttt gtaatcactt    10200
attgacttag caaagaagat gtaagtttat tcggtataag ttaataaaaa gtgaaacagt    10260
taaggcgggt tttcaaggaa tgatatactt agtaaaagaa tggaaggttg acaaagcat     10320 tgcgcctggc agaaaaagga acgatttgtt ttttgaacta gtatagagat ttcacttgag    10380
ctgagggcca ttacacacca actgtatatg tttcagctct gcaacagcat cgtcgtgatg    10440
gtcgtcattt gatctcctac ctcgaccgag tagctcatca accgagttat tttgcagtac    10500
atcaaacaaa tatgggtcgt ccattcccat catctgatag tctagatcca tccatactac    10560
cgtattttag tagcacatgg acacggagat cg                                  10592

<210> SEQ ID NO 5
<211> LENGTH: 5578
<212> TYPE: DNA
<213> ORGANISM: Artificial Sequence
<220> FEATURE:
<223> OTHER INFORMATION: Synthetic Consturct

<400> SEQUENCE: 5
gcggccgcgg gtgaggcttt gccaaggcat caatggatcc cgaggacatg ctgctcgcgt      60
cggtcctccg ccgctccctg acgatgtcgg agacagatgc gcggcggtgg gtggggcatt     120
ggcgaggcgc tggtggatct ggaggacatg ctcctcgtgt cggtcctccg ccgctcccctg    180 acgacggtag agacggatgc gcggtgatgg gtgaggcgtt ggggaggctc cggtggatcc     240
cgagaacacc ctcctcgcat cggtcccccg ctgcttgcta acgacggcgg agagggatgc     300
gcggcggcgg gtgaggcgtt ggagaggcgc tggtggatcc agaggacacg ctccttgtgc     360
ggatcctccg ccgctccctg atggcagcga agagggatgc gcggcggcgg gtgaggcgtt     420
ggggaggcgc cggtggatcc cgaggacacg ctcctcgcgt cggtctccgc cgctccctga     480
cgacgacgga gacggatgca cggcggcggg tgaggcgttg gcgaggcgtc ggtggatccc     540
gaagacacgc tcctcgcgtt ggtcctccgc tgctcgctga caatggcaga gagggatgcg     600
tggcggcggg tgaggcgttg gagaggcgtc gatggatccg gaggacacgc tcctcgtgtc     660
aatcctccgc cggtccctga tgacggcgga gaggggtgcg cggcggcggg tgaggcattg     720
gggaggcgct ggtggatccc gaggacatgc tcctcgcgtc ggtcctccgc tgccccctga     780
cgaaggcgaa gacggatgcg aggcgccggg tgaggcattg tcgaggcgtc ggtggatccc     840
gaggacacgc tcgtcaagtc agtcctccgc cgctccctgt cgacggtgga cacggtttca     900
tggcgatggg tgaggcgtcg gcaaacgcgt gcactggtgg atccttagga cacgctcgtt     960
acgtcggtcc tccgccgctc cctgacgatg gtggagactg atgcacggcg gctctggcat    1020
cgagctgtcc gagcacgagg caatggtgca agttgcggcg aaggcgaaca ccgaggagta    1080
ggagcgcttg ctccagggc tggccgcgca gatctcctcg gacggccatg accctccgac     1140
ggccaaggcc agcgcacgac cccaaacgga cgtccggttt ggcctgcttt cgtctgtttg    1200
cggcggcaat gggttcgccc atgtctgctt gggtccgttg ggttgtcgat atgcccaacg    1260
cacggccgca ccccaaaatca tgtccaggg ggacgtgatt aaaaaaacac aaaaactaaa    1320
atgaaatgcc aaaaaaatta aataaatgca agcataaaaa tataaaacat aaattaacca    1380
tcacggccac aaaacggccc agttccatgg ttcacataga cataattaac ataaaaacaa    1440
```

-continued

```
aataaaaccg ccgcccacgc gctcctgccg tgcccgtcgc cgtcttctca gtggccgccg    1500
ttgtcgtcgt tgtcgctgac gaggtcgacg tagtccggcg gcgtccagag gtgggacggc    1560
ggtgcgtggt acacgggggc gggctggaag gcgggaggtg cctacacctc ctcctcctgt    1620
ggcgacgcct cccgctccgg tgaccatggc gttgtggggc accagtccac tgctagccca    1680
ccaggcccgg gtggaacaca gccacgggct cctcctccat cacctcctcc gtcctcacca    1740
tctccagctc ggggatggcg acgtcgccgg ccgcagagag ggccatcatc tcttcgaggc    1800
cctcccattg gcgctcatcg tgcgtcttca tggagtcctc catgacacgt tgcatgagcc    1860
gggcctcctc ctccgctgtc atgcgaggag gtggtggtgg cagcggagat ggtgaaggcg    1920
acggcgtggg cgtgaggccg cgcacccgcg tacgcctgcg cacctgggga gcagccgctg    1980
cgcgctctcg acgtggccgt cgcggccccg acaaggtgcc ggcgaagaaa aaggcgcgac    2040
gcgtgtcgtg ctcgtcccga aaccacgtgt cccacaggtc ggagtcgggg gcgtaccgag    2100
ggtcgtagta caggtcgtcc ggcaggaggc ggcggcggca ctggatctcc tcgcggcgcg    2160
cacggccgct cgtcgggacc ggcgggatcg gcacccggtt ggcggagaga tgccagttat    2220
tggggaggtg cacgtcgctc catgggagcg gcgtcctcgt ctcccaataa cgccggcata    2280
catccgcgtg gatgtactgc tggtcgcgct tgccgccggc cgtagggccg atggtgaatg    2340
gggcaggcgt gggggctcga tgcggtggtg atgcgggctc ctctttcatg gagccgcggc    2400
ggcggcccga ggacaagcca gcctcgtggt cgcgcttccc cttgcgaccg gtgttccaga    2460
accccatggc tgcgaggcgg ccggccgacg agatcgagga cggggagagg gagagctagg    2520
gtttggggtg tgtcgggttt cgaggaggca gcacgggctg gagtggggag tgtggacgac    2580
gaccggtcca cggtttccca tttaagaagg acggcgactg tttgctggac ggatgacagg    2640
tggggccgac cgcgcgtgtg cattaatgtt ggctggtggg aggtaggtgg ccgcctgcta    2700
cgcggcctcg aggcggacga gcgacgcgtc cgtttgctgt ccgccgcgac ccaaatccgg    2760
cacatgtttg cgctcgaaat ggatcggccc ggacacaaaa cggaccagat aggttcaggc    2820
cgtcgcgcgc tgggcgtggg atttgttctt ttgtcccaaa tggacggggc cggacgggat    2880
ggggtcgcgc gcaagggcga gagcagaacc atcgaccgca agcggtgatt ttctgcgcac    2940
cttctgccat aggtgtagct cgtcgaccgc caagtatatc actgtctcgc gatttgagca    3000
tagagtcaat cgattttcct ggccaatggc gtcaagggga gagatttggt caaatgggcg    3060
gaagtcgcag acccatgtat atgtgcacgg gtgggtgggt gccttagggc atttacaacg    3120
caaggcgcta aggcgggcgc cagggtcagg atcctagtcg tttggcttag ttcccgtcca    3180
aatttgagaa ttgagctggc atcgatgcca tataagtcgt cgggcgtcgg gcgctaactc    3240
agttttctgt ctattttatg tgtgtagcgc tcatacgtgg ctctcagcgt tggaagaggg    3300
actcttagcc caggcgctag gaagaaaata ctattttatt tccagtcaag tgcctgatta    3360
ggcgccctcc attggagatg cccttatgtg cctctctacg ccgcagcagc cggaaactac    3420
ggcgcaccag tactggacgg ctcgtttctt attctaaaca cagatactag tgttgttgcc    3480
gccagtccct cgccgccgga gctctctctc tctctctccc tcgcacaaac atagaagaaa    3540
gaaggaagag gagcgatgca gtggacacaa caagctttac gcggtgcacg tacgctgccg    3600
gccgcacgaa cagccgatcg tttcattcc tgagctcgaa ctcagccacc ggacaacaac    3660
gagtacacag agggccttct atacccaagc tacacacatc aggctagcta ccacacgcaa    3720
gcacgcatgc atccactgca gcgaaagcta actactgca cgcatgcagc ccacgacccg    3780
gctgcatgac gcccgcgcct gccgagtcca cgatccgcac ggcgtgacca actaactgca    3840
```

```
tgcaactaga cggagcgccc acgcaacgcc cgccccgcgc tcctcagctc ccgcgcccgc    3900
cgcgcacgca cgccaacggg atacgactgg ttccagcgcc tggcgcggtc acacctcgcg    3960
cgtccgtcta accaacacac acacacatga ccccgccgcg cacccgccgc gcccgacacg    4020
cccggcgcaa tcgcggtggc ttatgcccaa cactcacccc ccttagccac gaattacagc    4080
aggtgagttc atcatcgtcg atgtcgccat ggccgtcgca tcgcaccgct gcggcctccg    4140
ccatgccgtc gacgtcgttg tagccgccgc cgtcctgacg tcgctgccac acctgccacc    4200
gtgccgccgt gcccttcgcg tgcactcccc gcgctcccgg cccgcgctcc cgcgcgcacg    4260
tacgctatct gcgcaactag gtccagtgtc tcgacgcggt ccactccac ggtcccgacg     4320 cgtctggtgc gcacccataa cacgcaccgg tcgcgcccgg ctcgccaccg cgtcttattg    4380
ccctgcactg ccgtgccgtc aaccgtagcg cagcgcctcc acggtcgtcg cgccgagccg    4440
ccgcggcctc tgcgacacca cgcaggtcct ccgcgacctc ctcgtctccg cgaccgccac    4500
tgctcgccgc gcgcacggca tcacgccaca ccgccgtgga ctcgccgcgc gttgccgacg    4560
ccacgcgctc gccgcacgcc cggcatcacg ccacaccgcc gtggactcgc gcgcgttgc    4620 cgagatcttc atgtccgccg cgcgccacgg ccgcccccg aacctgtggc tctgatacca    4680
aatgttgttg ccgccagtcc ctcgccgccg gagctctctc tctctctctc cctcgcacaa    4740
acatagaaga agaaggaag aggagcgatg cagtggacac aacaagcttt acgcggtgca    4800
cgtacgctgc cggccgcacg aacagccgat cgttttcatt cctgagctcg aactcagcca    4860
ccggacaaca acgagtacac agagggcctt ctatacccaa gctacacaca tcaggctagc    4920
taccacacgc aagcacgcat gcatccactg cagcgaaagc taactacatg cacgcatgca    4980
gcccacgacc cggctgcatg acgcccgcgc ctgccgagtc cacgatccgc acggcgtgac    5040
caactaactg catgcaacta dacggagcgc ccacgcaacg cccgccccgc gctcctcagc    5100
tcccgcgccc gccgcgcacg cacgccaacg ggatacgact ggttccagcg cctggcgcgg    5160
tcacacctcg cgcgtccgtc taaccaacac acacacacat gaccccgccg cgcacccgcc    5220
gcgcccgaca cgcccggcgc aatcgcggtg gcttatgccc aacaactagt gtgcacctcg    5280
ttgagagtgc ggcacccgac tgcacagtgc acatgcatgc agctggctct ttctcttgac    5340
ttgacacgct ctcgcttctc ccgattcctg cccgcgccgg cgtctccacc cgacttgatc    5400
gacatcggca tcggcatcgg cctcggcatc ggccctcga cgacgctcag tatataagcg    5460
atcgggctgg tggagctgct tgcagtaccc gcagtggaca cacgcttagc tttagctacg    5520
taggcgcagc agccggaaac tagctagcag gtcgagaagg ccggccggag gtagggag     5578
```

<210> SEQ ID NO 6
<211> LENGTH: 4681
<212> TYPE: DNA
<213> ORGANISM: Artificial Sequence
<220> FEATURE:
<223> OTHER INFORMATION: Synthetic Construct

<400> SEQUENCE: 6

```
cagtacccgc agtggacaca cgcttagctt tagctacgta ggcgcagcag ccggaaacta      60
gctagcaggt cgagaaggcc ggccggaggt agggagatgg cagggcacca cagcccctcg     120
gcggcctcgg cactgcgtga aaagacacg ctggtgaggt gtctcgtggg atcaggtccc     180
ggcggcggcg ctcatgccgg gaccttcggc gctgtgcggg acttcctcat ccagttccgc     240
gaccaaggaa tccctgggt ccgcatctac gagtcaaccc cggcttggca gcagcaatgt      300
```

```
gagtaatcta atctccactg ttgattgatc tgcataatgc tactcattct cactatcgcc    360
tggccggcct cgtgatcaac atgaatgcgc gcgtatgtta tgcagccggc gggctgctga    420
tccaggattg ggacggagac gccgcggcgg agggagccaa ggtgttcttc acgctcatca    480
ccacaaggag gggcggcgcc attaacagga gggcactggg aggcgggacg tggacaagca    540
aggccgcgcc cagggtaggg gacgaggtcg ccgtcagcac actgtacttc aaacggggcg    600
ggtcagcgg cagattattc accgccttgg agatccatct cagaaacgag gtatgctgtg    660
cttgctccat ccatcgcatt ttttttgttt tgttttaaat ttgcttatgc gactatatat    720
tatcatggtt gttgcccacg ttgttcaaag atttgcgccc ctgcttgaaa ctgctggtat    780
atatgaaccc ttttcttaag cttcggtgta ggactacggc tccgttcgtt ttttctcctt    840
ctctcgccaa aacaaattcc atctcaccga tctcttctcc gtcggcgacg aaccctagct    900
cggatcagtc cgcttccctt caaaaaaaag aaaataaaa atccatctca ctgaagttgc    960
atttcaacat tgctgttccg tacatctaaa cttacatatg acgacatgat caacagtaga   1020
ttagtccttt ttattatata taggatgatc ccaattcgtt tgttctctag ctagagcaat   1080
ataatactat aggatcagta cttttttaggg gcacaccacc ataaggttag tcctaagttg   1140
accttcttct gctgccctta aacctcgtcg tcatagccca gctagtaaac cctcgccctc   1200
ggtctgtttc ttacgagccc aagcagcccg ttccgtttcc tcacgagccc aagcccagct   1260
tgtaaaccct tccgtccccc gcctcgtctc gtccagtcca gacccctctt ctcttctagt   1320
caacggtcgc cggcggcggc ggcgccaagt catccaagac agagagcgct cagccgcagc   1380
cccgaaccct agaaatcaag cgaacgcggc ggcgaggttc cggttgggga gatgcacttc   1440
tttttttcagc aagtcagtga aaattatatg ttgatctttc gtgtttgttt ctgttttttct   1500
agccccaagt tgctatctgc ctgctgcatc cgactaacta tctgtatagc attcgggatt   1560
tgaggctcta catcgaccag gtaaatattt tctatttcca gttttggttt tcacccgtgg   1620
gcgctacttt caatgttcgg tctacaagcc aattagctac tgtagattga ttcagttgct   1680
gaacgataaa acaagaccga ttccactatg catgttttgc tacaaatgaa tgagcccaac   1740
aacattacta tgaggttact ctcctctttc agggatggtt cccggagga actcaagcaa     1800
acctgggcgc ggagcaatat caaggtattc ataagtcatg attgatcccc aatgccttcg   1860
acagtttaac tgaaacaggc accatctgta cttttgttga acatagtga tctttgatct    1920
gggtacatag atagccctga tttcatatat ctacgtcctt acattagtca tggaaatatg    1980
aaaacgaggt agattgatct gttatttat cctattactt agcattttg tacttgtaca     2040
tcttatttcg gcagataaat ttaaaacccc acagctgata tatatattat cctcaattta   2100
tacactattt gatgaattga taggtaaga actcataagt cgagaactct agatatatac    2160
cagggacgtc tactatcaga acacatgatt gaacataaat caatcactgc agaatgatat   2220
ttgaactaag cgtttatcag tcataagata gacatattgt tgttttccaa tatatattgt   2280
ggaatttaat ctgggctata tgtaatagct ccaattctct gcgctgtggc atattaaatc    2340
gcattggtct tacactggca gaagttttac atgctacctt gcttgcagat cctgatgttc   2400
ctggattcgt gagtggttca cgtgctgatt acaccactat tctgttttct agcagtgagg   2460
taattaagct ttccatgcac aaactagaac aagttaccac caaatttaga tttcttgtac   2520
aaccccctatg cttatctaaa tgtgacaact caagttctat tatctctagt aagaagacat   2580
agaagatgtt ttattaagtc aatttctgtt cttacgtact ccctctgtcc cacaatgtaa   2640
cacgtttaac gtcttgcatt gtgggacgga gggagagaac ttgtcatttg cttactggta   2700
```

-continued

```
ttggagttag actggtatac ttaattggga atcattttg aaaactaagg catcgagtcc   2760
ttcactgttc tgggtgtact gaggtaaaca acatgcactt cggatgagat gggagaatta   2820
ggctattagc actcaggatt agcctacaga taggttttat gcacagcaca acctatatat   2880
gagatatttt acataccgta tgatacctgt aaacattgat aagtggtata tctcaacacc   2940
atgcataatt aattgcaata ctacagaatg tactagacaa ttctggaccc tccgatttgg   3000
atctggcggc cgatatagtc cttctcccat gttgttttg ttatatagaa cacttgtttg    3060
gagtgaattt agcgtacatt atctggaact tcagttttg tctgttgata attggcttac    3120
agctgcattt cagaacataa caatgtgagt ttgaacagac tatttacgac cagcaatcga   3180
ttcattcctc cggggctgct ctgccacctc atgatgcatc tctggatgct atttctcacc   3240
acctgttttc agaaaacaac tcaacgccag aggtactata caattacatt catcctcggt   3300
cttgttgcat caccacattt tattttattt ttcagttgat ctacgatttc cgtgttttag   3360
ttgccacata tattgcaagt aaactgatct tatatttcct tttgcttgca gtttggtgga   3420
cagtattctc atgctgatga aatatcaatc cttaatgaat actacaatac cttgatgggg   3480
accaactcca actcaggatt gcatggtacg cttctttgct gttgaaataa gtggtaacgt   3540
aggaccaaca acattgcttt ttcaaaattt caagtagttt ggacctgaat acaagtaaga   3600
aaaagatgat ccttcagtgt tctgttctct tggctaaaa tgacaagtaa tttgcacctt    3660
tctcctgttt tggaatatta ttgttacaca cttgaatcca tagggtttta tagcaacttt   3720
ggaggatttt attccgttgg attgctcatg gatacccttg atcaaagtaa tgaccatcat   3780
aatttctatg aattgtattt tcctacaccc cttttcccgt aggattctac acaccaaaga   3840
attttgccgt tgttgtcaag tggtgttcac ctgcacgtgc taccttcaat gtttgttcca   3900
gaagccaatt aactacattg attcgtatga gcacacagta ctaagcctac taataggttt   3960
ttccacagca ctaccattgt taatatatat gtacatatga gatattgtgc atactgttat   4020
aaggttactg taaatatcga ttagtgatat gtccttgcaa aacaagaaga gaagtttgta   4080
gggccgtgtt ttagtcccac acatatgttg aaatcgagct gacctatgt tcccgttttt    4140
ttttgcagcc ttatccgcag cattctcaag ttgatgatac gtcatccccg gactacgact   4200
acaatccttt cggagagttt tgagattgag agatgacata tgagcagtgc tgtctgtaca   4260
tattatttct tgtacagttt ctaattatga actcttgaat aatcttgtcc cggtggacaa   4320
tgctgtatt tatgagtctt ggtaggaatg tatatgtttg gtataaaatc ggtgaagggt     4380
gcatgtagtg tatgacatcg ctttgacgga ggaggtgctg attgtacggg actgaactga   4440
aggcaagaca gcagcaagca agcactgaca acgtgtggat tgaatatagc tcagacggct   4500
gagagccgga ggtcatcagg cacgatgctc aacgccggag gtcaattgta attttatgt    4560
aatataattt gccctagtgt tgcaatatgt acaaatattt tagtatttta gcctgtgatt   4620
catcggtcca tattaatgtt attgtgtgaa taaatgttta tcaaatcctg cctgtgattt   4680
a                                                                   4681
```

<210> SEQ ID NO 7
<211> LENGTH: 10600
<212> TYPE: DNA
<213> ORGANISM: Artificial Sequence
<220> FEATURE:
<223> OTHER INFORMATION: Synthetic Construct

<400> SEQUENCE: 7

-continued

```
gcggccgcgg gtgaggcttt gccaaggcat caatggatcc cgaggacatg ctgctcgcgt      60
cggtcctccg ccgctccctg acgatgtcgg agacagatgc gcggcggtgg gtggggcatt     120
ggcgaggcgc tggtggatct ggaggacatg ctcctcgtgt cggtcctccg ccgctccctg     180
acgacggtag agacggatgc gcggtgatgg gtgaggcgtt ggggaggctc cggtggatcc     240
cgagaacacc ctcctcgcat cggtcccccg ctgcttgcta acgacggcgg agagggatgc     300
gcggcggcgg gtgaggcgtt ggagaggcgc tggtggatcc agaggacacg ctccttgtgc     360
ggatcctccg ccgctccctg atggcagcga agagggatgc gcggcggcgg gtgaggcgtt     420
ggggaggcgc cggtggatcc cgaggacacg ctcctcgcgt cggtctccgc cgctccctga     480
cgacgacgga gacggatgca cggcggcggg tgaggcgttg gcgaggcgtc ggtggatccc     540
gaagacacgc tcctcgcgtt ggtcctccgc tgctcgctga caatggcaga gagggatgcg     600
tggcggcggg tgaggcgttg gagaggcgtc gatggatccg gaggacacgc tcctcgtgtc     660
aatcctccgc cggtccctga tgacggcgga gaggggtgcg cggcggcggg tgaggcattg     720
gggaggcgct ggtggatccc gaggacatgc tcctcgcgtc ggtcctccgc tgcccctga      780
cgaaggcgaa gacggatgcg aggcgccggg tgaggcattg tcgaggcgtc ggtggatccc     840
gaggacacgc tcgtcaagtc agtcctccgc cgctccctgt cgacggtgga gacggtttca     900
tggcgatggg tgaggcgtcg gcaaacgcgt gcactggtgg atccttagga cacgctcgtt     960
acgtcggtcc tccgccgctc cctgacgatg gtggagactg atgcacgcg gctctggcat    1020
cgagctgtcc gagcacgagg caatggtgca agttgcggcg aaggcgaaca ccgaggagta    1080
ggagcgcttg ctccagggc tggccgcgca gatctcctcg gacggccatg accctccgac     1140
ggccaaggcc agcgcacgac cccaaacgga cgtccggttt ggcctgcttt cgtctgtttg    1200
cggcggcaat gggttcgccc atgtctgctt gggtccgttg ggttgtcgat atgcccaacg    1260
cacggccgca ccccaaatca tgtccagggt ggacgtgatt aaaaaaacac aaaaactaaa    1320
atgaaatgcc aaaaaaatta aataaatgca agcataaaaa tataaaacat aaattaacca    1380
tcacggccac aaaacggccc agttccatgg ttcacataga cataattaac ataaaaacaa    1440
aataaaaccg ccgcccacgc gctcctgccg tgcccgtcgc cgtcttctca gtggccgccg    1500
ttgtcgtcgt tgtcgctgac gaggtcgacg tagtccggcg gcgtccagag gtgggacggc    1560
ggtgcgtggt acacggggc gggctggaag gcgggaggtg cctacacctc ctcctcctgt    1620
ggcgacgcct cccgctccgg tgaccatggc gttgtggggc accagtccac tgctagccca    1680
ccaggccccgg gtgaacaca gccacgggct cctcctccat cacctcctcc gtcctcacca    1740
tctccagctc ggggatggcg acgtcgccgg ccgcagagag ggccatcatc tcttcgaggc    1800
cctcccattg gcgctcatcg tgcgtcttca tggagtcctc catgacacgt tgcatgagcc    1860
gggcctcctc ctccgctgtc atgcgaggag gtggtggtgg cagcggagat ggtgaaggcg    1920
acggcgtggg cgtgaggccg cgcacccgcg tacgcctgcg cacctgggga gcagccgctg    1980
cgcgctctcg acgtggccgt cgcggccccg acaaggtgcc ggcgaagaaa aaggcgcgac    2040
gcgtgtcgtg ctcgtcccga aaccacgtgt cccacaggtc ggagtcgggg cgtaccgag     2100
ggtcgtagta caggtcgtcc ggcaggaggc ggcggcggca ctggatctcc tcgcggcgcg    2160
cacggccgct cgtcgggacc ggcgggatcg gcacccggtt ggcggagaga tgccagttat    2220
tggggaggtg cacgtcgctc catgggagcg gcgtcctcgt ctcccaataa cgccggcata    2280
catccgcgtg gatgtactgc tggtcgcgct tgccgccggc cgtagggccg atggtgaatg    2340
gggcaggcgt gggggctcga tgcggtggtg atgcgggctc ctctttcatg gagccgcggc    2400
```

```
ggcggcccga ggacaagcca gcctcgtggt cgcgcttccc cttgcgaccg gtgttccaga    2460 acccatggc tgcgaggcgg ccggccgacg agatcgagga cggggagagg gagagctagg     2520
gtttggggtg tgtcgggttt cgaggaggca gcacgggctg gagtggggag tgtggacgac    2580
gaccggtcca cggtttccca tttaagaagg acggcgactg tttgctggac ggatgacagg    2640
tggggccgac cgcgcgtgtg cattaatgtt ggctggtggg aggtaggtgg ccgcctgcta    2700
cgcggcctcg aggcggacga gcgacgcgtc cgtttgctgt ccgccgcgac ccaaatccgg    2760
cacatgtttg cgctcgaaat ggatcggccc ggacacaaaa cggaccagat aggttcaggc    2820
cgtcgcgcgc tgggcgtggg atttgttctt ttgtcccaaa tggacggggc cggacgggat    2880
ggggtcgcgc gcaagggcga gagcagaacc atcgaccgca agcggtgatt ttctgcgcac    2940
cttctgccat aggtgtagct cgtcgaccgc caagtatatc actgtctcgc gatttgagca    3000
tagagtcaat cgattttcct ggccaatggc gtcaagggga gagatttggt caaatgggcg    3060
gaagtcgcag acccatgtat atgtgcacgg gtgggtgggt gccttagggc atttacaacg    3120
caaggcgcta aggcgggcgc cagggtcagg atcctagtcg tttggcttag ttcccgtcca    3180
aatttgagaa ttgagctggc atcgatgcca tataagtcgt cgggcgtcgg gcgctaactc    3240
agttttctgt ctattttatg tgtgtagcgc tcatacgtgg ctctcagcgt tggaagaggg    3300
actcttagcc caggcgctag gaagaaaata ctattttatt tccagtcaag tgcctgatta    3360
ggcgccctcc attggagatg cccttatgtg cctctctacg ccgcagcagc cggaaactac    3420
ggcgcaccag tactgacgg ctcgtttctt attctaaaca cagatactag tgttgttgcc     3480
gccagtccct cgccgccgga gctctctctc tctctctccc tcgcacaaac atagaagaaa    3540
gaaggaagag gagcgatgca gtggacacaa caagctttac gcggtgcacg tacgctgccg    3600
gccgcacgaa cagccgatcg ttttcattcc tgagctcgaa ctcagccacc ggacaacaac    3660
gagtacacag agggccttct atacccaagc tacacacatc aggctagcta ccacacgcaa    3720
gcacgcatgc atccactgca gcgaaagcta actacatgca cgcatgcagc ccacgacccg    3780
gctgcatgac gcccgcgcct gccgagtcca cgatccgcac ggcgtgacca actaactgca    3840
tgcaactaga cggagcgccc acgcaacgcc cgccccgcgc tcctcagctc ccgcgcccgc    3900
cgcgcacgca cgccaacggg atacgactgg ttccagcgcc tggcgcggtc acacctcgcg    3960
cgtccgtcta accaacacac acacacatga ccccgccgcg cacccgccgc gcccgacacg    4020
cccggcgcaa tcgcggtggc ttatgcccaa cactcacccc ccttagccac gaattacagc    4080
aggtgagttc atcatcgtcg atgtcgccat ggccgtcgca tcgcaccgct gcggcctccg    4140
ccatgccgtc gacgtcgttg tagccgccgc cgtcctgacg tcgctgccac acctgccacc    4200
gtgccgccgt gccttcgcg tgcactcccc gcgctcccgg ccgcgctcc cgcgcgcacg      4260 tacgctatct gcgcaactag gtccagtgtc tcgacgcggt ccactcccac ggtcccgacg    4320
cgtctggtgc gcacccataa cacgcaccgg tcgcgcccgg ctcgccaccg cgtcttattg    4380
ccctgcactg ccgtgccgtc aaccgtagcg cagcgcctcc acggtcgtcg cgccgagccg    4440
ccgcggcctc tgcgacacca cgcaggtcct ccgcgacctc ctcgtctccg cgaccgccac    4500
tgctcgccgc gcgcacggca tcacgccaca ccgccgtgga ctcgccgcgc gttgccgacg    4560
ccacgcgctc gccgcacgcc cggcatcacg ccacaccgcc gtggactcgc cgcgcgttgc    4620
cgagatcttc atgtccgccg cgcgccacgg ccgcccccg aacctgtggc tctgataccca    4680 aatgttgttg ccgccagtcc ctcgccgccg gagctctctc tctctctctc cctcgcacaa    4740
```

```
acatagaaga aagaaggaag aggagcgatg cagtggacac aacaagcttt acgcggtgca    4800
cgtacgctgc cggccgcacg aacagccgat cgttttcatt cctgagctcg aactcagcca    4860
ccggacaaca acgagtacac agagggcctt ctatacccaa gctacacaca tcaggctagc    4920
taccacacgc aagcacgcat gcatccactg cagcgaaagc taactacatg cacgcatgca    4980
gcccacgacc cggctgcatg acgcccgcgc ctgccgagtc cacgatccgc acggcgtgac    5040
caactaactg catgcaacta gacggagcgc ccacgcaacg cccgccccgc gctcctcagc    5100
tcccgcgccc gccgcgcacg cacgccaacg ggatacgact ggttccagcg cctggcgcgg    5160
tcacacctcg cgcgtccgtc taaccaacac acacacacat gaccccgccg cgcacccgcc    5220
gcgcccgaca cgcccggcgc aatcgcggtg gcttatgccc aacaactagt gtgcacctcg    5280
ttgagagtgc ggcacccgac tgcacagtgc acatgcatgc agctggctct ttctcttgac    5340
ttgacacgct ctcgcttctc ccgattcctg cccgcgccgg cgtctccacc cgacttgatc    5400
gacatcggca tcggcatcgg cctcggcatc ggcccctcga cgacgctcag tatataagcg    5460
atcgggctgg tggagctgct tgcagtaccc gcagtggaca cacgcttagc tttagctacg    5520
taggcgcagc agccggaaac tagctagcag gtcgagaagg ccggccggag gtagggagat    5580
ggcagggcac cacagcccct cggcggcctc ggcactgcgt gaaaaagaca cgctggtgag    5640
gtgtctcgtg ggatcaggtc ccggcggcgg cgctcatgcc gggaccttcg gcgctgtgcg    5700
ggacttcctc atccagttcc gcgaccaagg aatcccctgg gtccgcatct acgagtcaac    5760
cccggcttgg cagcagcaat gtgagtaatc taatctccac tgttgattga tctgcataat    5820
gctactcatt ctcactatcg cctggccggc ctcgtgatca acatgaatgc gcgcgtatgt    5880
tatgcagccg gcgggctgct gatccaggat tgggacggag acgccgcggc ggagggagcc    5940
aaggtgttct tcacgctcat caccacaagg aggggcggcg ccattaacag gagggcactg    6000
ggaggcggga cgtggacaag caaggccgcg cccagggtag gggacgaggt cgccgtcagc    6060
acactgtact tcaaacgggg cgggtccagc ggcagattat tcaccgcctt ggagatccat    6120
ctcagaaacg aggtatgctg tgcttgctcc atccatcgca tttttttttgt tttgttttaa    6180 atttgcttat gcgactatat attatcatgg ttgttgccca cgttgttcaa agatttgcgc    6240
ccctgcttga aactgctggt atatatgaac ccttttctta agcttcggtg taggactacg    6300
gctccgttcg ttttttctcc ttctctcgcc aaaacaaatt ccatctcacc gatctcttct    6360
ccgtcggcga cgaaccctag ctcggatcag tccgcttccc ttcaaaaaaa agaaaaataa    6420
aaatccatct cactgaagtt gcatttcaac attgctgttc cgtacatcta aacttacata    6480
tgacgacatg atcaacagta gattagtcct ttttattata tataggatga tcccaattcg    6540
tttgttctct agctagagca atataatact ataggatcag tacttttttag gggcacacca    6600 ccataaggtt agtcctaagt tgaccttctt ctgctgccct taaacctcgt cgtcatagcc    6660
cagctagtaa accctcgccc tcggtctgtt tcttacgagc ccaagcagcc cgttccgttt    6720
cctcacgagc ccaagcccag cttgtaaacc cttccgtccc ccgcctcgtc tcgtccagtc    6780
cagacccctc ttctcttcta gtcaacggtc gccggcggcg gcggcgccaa gtcatccaag    6840
acagagagcg ctcagccgca gccccgaacc ctagaaatca agcgaacgcg gcggcgaggt    6900
tccggttggg gagatgcact tctttttttca gcaagtcagt gaaaattata tgttgatctt    6960 tcgtgttttgt ttctgttttt ctagccccaa gttgctatct gcctgctgca tccgactaac    7020
tatctgtata gcattcggga tttgaggctc tacatcgacc aggtaaatat tttctatttc    7080
cagttttggt tttcacccgt gggcgctact ttcaatgttc ggtctacaag ccaattagct    7140
```

```
actgtagatt gattcagttg ctgaacgata aaacaagacc gattccacta tgcatgtttt    7200
gctacaaatg aatgagccca acaacattac tatgaggtta ctctcctctt tcagggatgg    7260
ttcccgggag gaactcaagc aaacctgggc gcggagcaat atcaaggtat tcataagtca    7320
tgattgatcc ccaatgcctt cgacagttta actgaaacag gcaccatctg tacttttgtt    7380
gaaacatagt gatctttgat ctgggtacat agatagccct gatttcatat atctacgtcc    7440
ttacattagt catggaaata tgaaaacgag gtagattgat ctgttatttt atcctattac    7500
ttagcatttt tgtacttgta catcttattt cggcagataa atttaaaacc ccacagctga    7560
tatatatatt atcctcaatt tatacactat ttgatgaatt gataaggtaa gaactcataa    7620
gtcgagaact ctagatatat accagggacg tctactatca gaacacatga ttgaacataa    7680
atcaatcact gcagaatgat atttgaacta agcgtttatc agtcataaga tagacatatt    7740
gttgttttcc aatatatatt gtggaattta atctgggcta tatgtaatag ctccaattct    7800
ctgcgctgtg gcatattaaa tcgcattggt cttacactgg cagaagtttt acatgctacc    7860
ttgcttgcag atcctgatgt tcctggattc gtgagtggtt cacgtgctga ttacaccact    7920
attctgtttt ctagcagtga ggtaattaag ctttccatgc acaaactaga acaagttacc    7980
accaaattta gatttcttgt acaaccccta tgcttatcta aatgtgacaa ctcaagttct    8040
attatctcta gtaagaagac atagaagatg ttttattaag tcaatttctg ttcttacgta    8100
ctccctctgt cccacaatgt aacacgttta acgtcttgca ttgtgggacg gagggagaga    8160
acttgtcatt tgcttactgg tattggagtt agactggtat acttaattgg gaaatcattt    8220
tgaaaactaa ggcatcgagt ccttcactgt tctgggtgta ctgaggtaaa caacatgcac    8280
ttcggatgag atgggagaat taggctatta gcactcagga ttagcctaca gataggtttt    8340
atgcacagca caacctatat atgagatatt ttacataccg tatgatacct gtaaacattg    8400
ataagtggta tatctcaaca ccatgcataa ttaattgcaa tactacagaa tgtactagac    8460
aattctggac cctccgattt ggatctggcg gccgatatag tccttctccc atgttgtttt    8520
tgttatatag aacacttgtt tggagtgaat ttagcgtaca ttatctggaa cttcagtttt    8580
tgtctgttga taattggctt acagctgcat ttcagaacat aacaatgtga gtttgaacag    8640
actatttacg accagcaatc gattcattcc tccggggctg ctctgccacc tcatgatgca    8700
tctctggatg ctatttctca ccacctgttt tcagaaaaca actcaacgcc agaggtacta    8760
tacaattaca ttcatcctcg gtcttgttgc atcaccacat tttatttat ttttcagttg    8820 atctacgatt tccgtgtttt agttgccaca tatattgcaa gtaaactgat cttatatttc    8880
cttttgcttg cagtttggtg gacagtattc tcatgctgat gaaatatcaa tccttaatga    8940
atactacaat accttgatgg ggaccaactc caactcagga ttgcatggta cgcttctttg    9000
ctgttgaaat aagtggtaac gtaggaccaa caacattgct ttttcaaaat ttcaagtagt    9060
ttggacctga atacaagtaa gaaaaagatg atccttcagt gttctgttct ctttggctaa    9120
aatgacaagt aatttgcacc tttctcctgt tttggaatat tattgttaca cacttgaatc    9180
catagggttt tatagcaact ttggaggatt ttattccgtt ggattgctca tggataccct    9240
tgatcaaagt aatgaccatc ataatttcta tgaattgtat tttcctacac cccttttccc    9300
gtaggattct acacaccaaa gaattttgcc gttgttgtca agtggtgttc acctgcacgt    9360
gctaccttca atgtttgttc cagaagccaa ttaactacat tgattcgtat gagcacacag    9420
tactaagcct actaataggt ttttccacag cactaccatt gttaatatat atgtacatat    9480
```

-continued

```
gagatattgt gcatactgtt ataaggttac tgtaaatatc gattagtgat atgtccttgc    9540
aaaacaagaa gagaagtttg tagggccgtg ttttagtccc acacatatgt tgaaatcgag    9600
ctgaccttat gttcccgttt ttttttgcag ccttatccgc agcattctca agttgatgat    9660
acgtcatccc cggactacga ctacaatcct ttcggagagt tttgagattg agagatgaca    9720
tatgagcagt gctgtctgta catattattt cttgtacagt ttctaattat gaactcttga    9780
ataatcttgt cccggtggac aatgctgtat tttatgagtc ttggtaggaa tgtatatgtt    9840
tggtataaaa tcggtgaagg gtgcatgtag tgtatgacat cgctttgacg gaggaggtgc    9900
tgattgtacg ggactgaact gaaggcaaga cagcagcaag caagcactga caacgtgtgg    9960
attgaatata gctcagacgg ctgagagccg gaggtcatca ggcacgatgc tcaacgccgg   10020
aggtcaattg taattttat gtaatataat ttgccctagt gttgcaatat gtacaaatat   10080
tttagtattt tagcctgtga ttcatcggtc catattaatg ttattgtgtg aataaatgtt   10140
tatcaaatcc tgcctgtgat ttatctgccc atgttttagg attttatttt gtaatcactt   10200
attgacttag caaagaagat gtaagtttat tcggtataag ttaataaaaa gtgaaacagt   10260
taaggcgggt tttcaaggaa tgatatactt agtaaaagaa tggaaggttg gacaaagcat   10320
tgcgcctggc agaaaaagga acgatttgtt ttttgaacta gtatagagat ttcacttgag   10380
ctgagggcca ttacacacca actgtatatg tttcagctct gcaacagcat cgtcgtgatg   10440
gtcgtcattt gatctcctac ctcgaccgag tagctcatca accgagttat tttgcagtac   10500
atcaaacaaa tatgggtcgt ccattcccat catctgatag tctagatcca tccatactac   10560
cgtattttag tagcacatgg acacggagat cgggcgcgcc                         10600
```

<210> SEQ ID NO 8
<211> LENGTH: 22
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-RP1

<400> SEQUENCE: 8
aggtttgctt gagttcctcc cg                                              22

<210> SEQ ID NO 9
<211> LENGTH: 22
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-RP2

<400> SEQUENCE: 9
ccttgtggtg atgagcgtga ag                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-FP1

<400> SEQUENCE: 10
cgggaggaac tcaagcaaac ct                                          22

<210> SEQ ID NO 11
<211> LENGTH: 22
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-FP2

<400> SEQUENCE: 11
gagtggttca cgtgctgatt ac                                          22

<210> SEQ ID NO 12
<211> LENGTH: 19
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-FP3

<400> SEQUENCE: 12
cagtacccgc agtggacac                                              19

<210> SEQ ID NO 13
<211> LENGTH: 26
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-RP3

<400> SEQUENCE: 13
taaatcacag gcaggatttg ataaac                                      26

<210> SEQ ID NO 14
<211> LENGTH: 21
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-FP4

<400> SEQUENCE: 14
ccgtcagcac actgtacttc a                                           21

<210> SEQ ID NO 15
<211> LENGTH: 20
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-FP4

<400> SEQUENCE: 15
cgatgtagag cctcaaatcc                                             20

```
<210> SEQ ID NO 16
<211> LENGTH: 21
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-RP5

<400> SEQUENCE: 16
cacatgtttg cgctcgaaat g                                              21

<210> SEQ ID NO 17
<211> LENGTH: 20
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-FP5

<400> SEQUENCE: 17
aagaaacgag ccgtccagta                                                20

<210> SEQ ID NO 18
<211> LENGTH: 23
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-FP6

<400> SEQUENCE: 18
cgcagtggac acacgcttag ctt                                            23

<210> SEQ ID NO 19
<211> LENGTH: 22
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-RP6

<400> SEQUENCE: 19
tgagttggag ttggtcccca tc                                             22

<210> SEQ ID NO 20
<211> LENGTH: 21
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-FP7

<400> SEQUENCE: 20
tctcagaaac gagccccaag t                                              21

<210> SEQ ID NO 21
<211> LENGTH: 20
<212> TYPE: DNA
```

<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-RP7

<400> SEQUENCE: 21
gaaccatccc tggtcgatgt                                              20

<210> SEQ ID NO 22
<211> LENGTH: 23
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WWMS-FP8

<400> SEQUENCE: 22
ggctctgata ccaaatgttg ttg                                          23

<210> SEQ ID NO 23
<211> LENGTH: 22
<212> TYPE: DNA
<213> ORGANISM: Artificial Sequence
<220> FEATURE:
<223> OTHER INFORMATION: Synthetic  PCR Primer
<220> FEATURE:
<221> NAME/KEY: misc_feature
<223> OTHER INFORMATION: WMS-FP8

<400> SEQUENCE: 23
atggtggtgt gcccctaaaa ag                                           22

<210> SEQ ID NO 24
<211> LENGTH: 23
<212> TYPE: DNA
<213> ORGANISM: Artificial Sequence
<220> FEATURE:
<223> OTHER INFORMATION: Synthetic PCR Primer

<400> SEQUENCE: 24
gcttgaaact gctggtatat atg                                          23

<210> SEQ ID NO 25
<211> LENGTH: 22
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-RP9

<400> SEQUENCE: 25
gtaatcagca cgtgaaccac tc                                           22

<210> SEQ ID NO 26
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 26
tgttcctgga ttcgtgagtg g                                            21

<210> SEQ ID NO 27
<211> LENGTH: 23
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-RP10

<400> SEQUENCE: 27
cgatctccgt gtccatgtgc tac                                              23

<210> SEQ ID NO 28
<211> LENGTH: 27
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-FP11

<400> SEQUENCE: 28
gcggccgcgg gtgaggcttt gccaagg                                          27

<210> SEQ ID NO 29
<211> LENGTH: 31
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-RP11

<400> SEQUENCE: 29
ggcgcgcccg atctccgtgt ccatgtgcta c                                     31

<210> SEQ ID NO 30
<211> LENGTH: 22
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: WMS-RP12

<400> SEQUENCE: 30
cgtagatgcg gacccagggg at                                               22

<210> SEQ ID NO 31
<211> LENGTH: 20
<212> TYPE: DNA
<213> ORGANISM: Artificial Sequence
<220> FEATURE:
<223> OTHER INFORMATION: Sythetic PCR Primer
<220> FEATURE:
<221> NAME/KEY: misc_feature
<223> OTHER INFORMATION: BAR-FP1

<400> SEQUENCE: 31
aagcacggtc aacttccgta                                                  20

<210> SEQ ID NO 32
<211> LENGTH: 20

```
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: BAR-RP1

<400> SEQUENCE: 32
gaagtccagc tgccagaaac                                        20

<210> SEQ ID NO 33
<211> LENGTH: 20
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: Actin-FP1

<400> SEQUENCE: 33
tcagccatac tgtgccaatc                                        20

<210> SEQ ID NO 34
<211> LENGTH: 18
<212> TYPE: DNA
<213> ORGANISM: Artificial Sequence
<220> FEATURE:
<223> OTHER INFORMATION: Sythetic PCR Primer
<220> FEATURE:
<221> NAME/KEY: misc_feature
<223> OTHER INFORMATION: Actin-FP1

<400> SEQUENCE: 34
cttcatgctg cttggtgc                                          18

<210> SEQ ID NO 35
<211> LENGTH: 20
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: Actin-FP2

<400> SEQUENCE: 35
gccatgtacg tcgcaattca                                        20

<210> SEQ ID NO 36
<211> LENGTH: 26
<212> TYPE: DNA
<213> ORGANISM: Artificial Sequence
<220> FEATURE:
<223> OTHER INFORMATION: Synthetic PCR Primer
<220> FEATURE:
<221> NAME/KEY: misc_feature
<223> OTHER INFORMATION: Actin-RP2

<400> SEQUENCE: 36
agtcgagaac gataccagta gtacga                                 26

<210> SEQ ID NO 37
<211> LENGTH: 49
```

```
<212> TYPE: DNA
<213> ORGANISM: Artificial Sequence
<220> FEATURE:
<223> OTHER INFORMATION: Synthetic Construct

<400> SEQUENCE: 37
tagggagagg cgcgccgacc cagctttctt gtacaaagtg gtgatcatg       49
```